US010619220B2

(12) United States Patent
Exner et al.

(10) Patent No.: US 10,619,220 B2
(45) Date of Patent: *Apr. 14, 2020

(54) DIRECT AMPLIFICATION AND DETECTION OF VIRAL AND BACTERIAL PATHOGENS

(71) Applicant: Quest Diagnostics Investments Incorporated, Wilmington, DE (US)

(72) Inventors: Maurice Exner, San Clemente, CA (US); Luca Jacky, Orange, CA (US); Yin-Peng Chen, Yorba Linda, CA (US); Huong Mai, Irvine, CA (US); Michelle M. Tabb, Santa Ana, CA (US); Michael Aye, Huntington Beach, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 318 days.

This patent is subject to a terminal disclaimer.

(21) Appl. No.: 15/288,291

(22) Filed: Oct. 7, 2016

(65) Prior Publication Data

US 2017/0081735 A1  Mar. 23, 2017

Related U.S. Application Data

(63) Continuation of application No. 14/130,705, filed as application No. PCT/US2012/045763 on Jul. 6, 2012, now Pat. No. 9,464,331.

(60) Provisional application No. 61/505,055, filed on Jul. 6, 2011, provisional application No. 61/552,405, filed on Oct. 27, 2011.

(51) Int. Cl.
| C12Q 1/70 | (2006.01) |
| C12Q 1/68 | (2018.01) |
| C12Q 1/686 | (2018.01) |
| C12Q 1/689 | (2018.01) |
| C12Q 1/6844 | (2018.01) |
| C12N 15/00 | (2006.01) |

(52) U.S. Cl.
CPC .............. *C12Q 1/701* (2013.01); *C12Q 1/68* (2013.01); *C12Q 1/686* (2013.01); *C12Q 1/689* (2013.01); *C12Q 1/6846* (2013.01); *C12Q 1/70* (2013.01)

(58) Field of Classification Search
CPC ....................... C12Q 2527/125; C12Q 1/6846; C12Q 1/686; C12Q 2527/101; C12Q 1/68; C12Q 1/689; C12Q 1/70; C12Q 1/701

See application file for complete search history.

(56) References Cited

U.S. PATENT DOCUMENTS

| 5,501,963 A | 3/1996 | Burckhardt |
| 6,242,235 B1 | 6/2001 | Schultz et al. |
| 6,767,723 B2 | 7/2004 | Tonoike |
| 6,962,780 B2 | 11/2005 | Nakayama et al. |
| 7,312,053 B2 | 12/2007 | Tada et al. |
| 7,575,864 B2 | 8/2009 | Bedzyk et al. |
| 7,727,718 B2 | 6/2010 | Chomczynski |
| 2002/0142402 A1 | 10/2002 | Tonoike |
| 2004/0259115 A1 | 12/2004 | Schuster et al. |
| 2010/0015621 A1 | 1/2010 | Chang et al. |
| 2013/0022963 A1 | 1/2013 | Exner et al. |

FOREIGN PATENT DOCUMENTS

| EP | 2 025 761 A1 | 2/2009 | |
| JP | 2011-019505 A | 2/2011 | |
| JP | 2012-050391 A | 3/2012 | |
| WO | WO-2004/018998 A2 | 3/2004 | |
| WO | WO-2006/138444 A2 | 12/2006 | |
| WO | WO-2009/016652 A1 | 2/2009 | |
| WO | WO-2010/065924 A1 | 6/2010 | |
| WO | WO-2010062897 A1 * | 6/2010 | ............. C12Q 1/689 |
| WO | WO-2010/116290 A1 | 10/2010 | |
| WO | WO-2011/121454 A2 | 10/2011 | |

OTHER PUBLICATIONS

Kai, E. et al., Detection of PCR products of *Escherichia coli* O157:H7 in human stool samples using surface plasmon resonance (SPR), FEMS Immunol. Med. Microbiol., vol. 29, pp. 283-288. (Year: 2000).*

McFarland, L. et al., Rectal Swab Cultures for Clostridium difficile Surveillance Studies, J. Clin. Microbiol., vol. 25, pp. 2241-2242 (Year: 1987).*

Rupnik, M. et al., Clostridium difficile infection: new developments in epidemiology and pathogenesis, Nature Rev., Microbiol., vol. 7 , pp. 526-536 (Year: 2009).*

Al-Soud et al., "Effects of Amplification Facilitators on Diagnostic PCR in the Presence of Blood, Feces and Meat," Journal of Clinical Microbiology, Dec. 2000, 38(12):4463-4470.

Demeke et al., "The effects of plant polysaccharides and buffer additives on PCR," Biotecnhiques, Mar. 1992, 12(3):332-334, Abstract only.

Hirsch et al., "Two-Centre Study Comparing DNA Preparation and PCR Amplification Protocols for Herpes Simplex Virus Detection in Cerebrospinal Fluids of Patients with Suspected Herpes Simplex Encephalitis," Journal of Medical Virology, 1999, 57:31-35.

KOMA Biotech Inc., EzWay™ Direct PCR Buffer, Instruction Manual, Catalog Nos. K0568001, K0568002, date unknown, 10 pages.

Loessner et al., "A New Procedure for Efficient Recovery of DNA, RNA, and Proteins from Listerial Cells by Rapid Lysis with a Recombinant Bacteriophage Endolysin," Applied and Environmental Microbioloty, Mar. 1995, 61(3):1150-1152.

(Continued)

*Primary Examiner* — Teresa E Strzelecka
(74) *Attorney, Agent, or Firm* — Foley & Lardner LLP

(57) ABSTRACT

Provided herein are methods for identifying the presence or absence of a target nucleic acid from a microorganism using direct amplification without a step of extraction of the nucleic acids, but retaining substantially the same specificity and sensitivity of methods assaying extracted nucleic acids.

12 Claims, 12 Drawing Sheets

Specification includes a Sequence Listing.

(56) References Cited

OTHER PUBLICATIONS

Pandori et al., "Real-Time PCR for detection of herpes simplex virus without nucleic acid extraction," BMC Infectious Diseases, 2006, 6:104, 9 pages.

Park et al., "Direct STR Amplification from Whole Blood and Blood-or Saliva-Spotted FTA® without DNA Purification," J. Forensic Sci., Mar. 2008, 53(2):335-341.

Pastorino et al., "Development of a TaqMan® RT-PCR assay without RNA extraction step for the detection and quantification of African Chikungunya viruses," Journal of Virological Methods, 2005, 124:65-71.

Ririe et al., "Product Differentiation by Analysis of DNA Melting Curves during the Polymerase Chain Reaction," Analytical Biochemistry, 1997, 245:154-160.

Sakai et al., "Quick detection of herpes viruses from skin vesicles and exudates without nucleic acid extraction using multiplex PCR," BioScience Trends, 2008, 2(4):164-168.

Tyagi et al., "Molecular beacons: Probes that fluoresce upon hybridization" Nature Biotechnol. (1996) 14:303-308.

Varadaraj et al., "Denaturants or cosolvents improve the specificity of PCR amplification of a G + C-rich DNA using genetically engineered DNA polymerases," Gene, Mar. 11, 1994, 140(1):1-5, Abstract only.

Yang et al., "A novel buffer system, AnyDirect, can improve polymerase chain reaction from whole blood without DNA isolation," Clinica Chimica Acta, 2007, 280:112-117.

Yang et al., "Direct Detection of *Shigella flexneri* and *Salmonella typhimurium* in Human Feces by Real-Time PCR," J. Microbiol. Biotechnol., 2007, 17(10):1616-1621.

Zhang et al., "Dircet DNA Amplification from Crude Clinical Samples Using a PCR Enhancer Cocktail and Novel Mutants of Taq," Journal of Molecular Diagnostics, vol. 12, No. 2, pp. 152-161, Mar. 2010.

Nix et al., "Sensitive, Seminested PCR Amplification of VP1 Sequences for Direct Identification of All Enterovirus Serotypes from Original Clinical Specimens," Journal of Clinical Microbiology, vol. 44, No. 8, pp. 2698-2704, Aug. 2006.

International Search Report issued in application No. PCT/US2012/45763 dated Jan. 23, 2013.

Promega, "GoTaq® DNA Polymerase," Product Bulletin, 2008.

Siednienko et al., "Expression Analysis of the Toll-Like Receptors in Human Peripheral Blood Mononuclear Cells," Methods in Molecular Biology, vol. 517, McCoy and O'Neill, eds., Chapter 1, pp. 3-14, 2009.

Zhang et al., "Detection of *Streptococcus pneumoniae* in Whole Blood by PCR," Journal of Clinical Microbiology, vol. 33, No. 3, pp. 596-601, Mar. 1995.

Ochert et al., "Inhibitory effect of salivary fluids on PCR: potency and removal," Genome Research, vol. 3, pp. 365-368, 1994.

Office Action issued in U.S. Appl. No. 13/543,336 dated Apr. 10, 2013.

Office Action issued in U.S. Appl. No. 13/543,336 dated Feb. 5, 2014.

Office Action issued in U.S. Appl. No. 13/543,336 dated Sep. 6, 2013.

Morita et al., "Rapid Detection of Virus Genome From Imported Dengue Fever and Dengue Hemorrahagic Fever Patients by Direct Polymerase Chain Reaction," Journal of Medicinal Virology, vol. 44, pp. 54-58, 1994.

Chang et al., "Tissue blot immunoassay and direct RT-PCR of cucumoviruses and potyviruses from the same NitroPure nitrocellulose membrane," Journal of Virological Methods, vol. 171, pp. 345-351, 2011.

Kerdsin et al., "Development of Triplex SYBR Green Real-Time PCR for Detecting Mycoplasma pneumoniae, Chlamydophila pneumoniae, and *Legionella* spp. Without Extraction of DNA," J. Inf. Dis., pp. 173-180, Jan. 1, 2010.

Liguori et al., "Rapid identification of *Candida* species in oral rinse solutions by PCR," Journal of Clinical Pathology, vol. 60, No. 9, pp. 1035-1039, Nov. 14, 2006.

Bae et al., "Characterization of DNA polymerase from the hyperthermophilic archaeon Thermococcus marinus and its application to PCR," Extremophiles; Life under Extreme Conditions, vol. 13, No. 4, pp. 657-667, May 3, 2009.

Giacomazzi et al., "Comparison of three 1-16 methods of DNA extraction from cold-smoked salmon and impact of physical treatments," Journal of Applied Microbiology, vol. 98, No. 5, pp. 1230-1238, May 1, 2005.

Supplementary European Search Report dated Jan. 14, 2015 in application No. EP 12 80 7070.

Office Action dated Aug. 28, 2015 in U.S. Appl. No. 14/130,705.

Office Action dated Nov. 16, 2015 in U.S. Appl. No. 14/130,705.

Office Action dated May 2, 2016 in U.S. Appl. No. 14/130,705.

Notice of Allowance dated Jun. 6, 2016 in U.S. Appl. No. 14/130,705.

Xinjian et al., Eds., Molecular Diagnostics, China Medical Science and Technology Press, Feb. 2010, p. 76, with English translation.

Supplementary European Search Report dated Apr. 12, 2019 in EP 18197921.2.

\* cited by examiner

SEQUENCE LISTING

<160> NUMBER OF SEQ ID NOS: 31

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgctcaccg tgcccagtga gcgt                                           24

<210> SEQ ID NO 2
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 2
ggcattttgg acaaagcgtc ta                                               22

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcttgtcacc tctgactaag gggat                                            25

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(7)
<223> OTHER INFORMATION: Inosine

<400> SEQUENCE: 4
ccgcggnatt gcaaaggatg taatggaagt gccgcgg                               37

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: Inosine

<400> SEQUENCE: 5
gagctgaatt tcccatngag ct                                               22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agctgcaaag caacattgga g                                                21

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```
acgcgcttca cgaaggctcc acatacacag cgcgt       35

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttttctagga cattgtaytg aacag       25

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcaaatatgg aaacatacgt gaacaa       26

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgcgcttgg ggcgacagtc acgtcgcgcg t       31

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgtcgaca atggcggaa       19

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcagcgacc ccgttagc       18

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agcggcccgg gtgcccggcc agccgct       27

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 14
gaggacgagc tggcctttc                                              19

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 15
acgcgcttcc gggcgttccg cgagcgcgt                                   29

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 16
gaggacgagc tggcctttc                                              19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 17
ggtggtggac aggtcgtaga g                                           21

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 18
acgcggcttc tgttgtttcg accgcgt                                     27

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 19
ccccgcttta acacattcca                                             20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcagttgcaa accgggat                                                18

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aggccacacg gacacccaaa gtagtcggtg gcct                               34

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cccctgaatg cggctaatc                                               19

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caattgtcac cataagcagc ca                                           22

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aggcagctca ccatcaataa taactgaacc agttgctgcc t                      41

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggttagattt agatgaaaag agatattatt tta                               33

```
<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
actaatcact aattgagctg tatcagga                                            28

<210> SEQ ID NO 27
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
ggttagattt agatgaaaag agatattatt ttacagatga atatattgca gcaactggtt         60
cagttattat tgatggtgag gagtattatt ttgatcctga tacagctcaa ttagtgatta        120
gt                                                                      122

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agcggcactc caaaaatcag cagctatcaa agcaggtgtg ccgct                         45

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagcttaata tcttctgcgc ttcgt                                               25

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
taacccagta tttgccgatc aa                                                  22

<210> SEQ ID NO 31
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
```

```
taacccagta tttgccgatc aaaactttgc tcgtaacgaa aaagaagcaa aagatagcgc        60
tatcacattt atccaaaaat cagcagctat caaagcaggt gcacgaagcg cagaagatat       120
taagctt                                                                 127
```

DIRECT AMPLIFICATION AND DETECTION OF VIRAL AND BACTERIAL PATHOGENS

CROSS-REFERENCE TO RELATED APPLICATIONS

This application is a continuation of U.S. patent application Ser. No. 14/130,705, filed May, 2014, now U.S. Pat. No. 9,464,331, which is a U.S. national stage of PCT/US2012/045763 filed Jul. 6, 2012, which claims the benefit under 35 U.S.C. § 119(e) to U.S. Provisional Application No. 61/505,055, filed Jul. 6, 2011 and U.S. Provisional Application Ser. No. 61/552,405, filed Oct. 27, 2011. The disclosures of each of the prior applications are considered part of and are incorporated by reference in the disclosure of this application.

FIELD OF THE INVENTION

The present invention relates to diagnostic and detection methods for viral and bacterial pathogen nucleic acids using direct amplification.

BACKGROUND OF THE INVENTION

The following discussion of the background of the invention is merely provided to aid the reader in understanding the invention and is not admitted to describe or constitute prior art to the present invention.

Clinical detection of viruses is usually accomplished using any one of a variety of methods. For example, virus particles or nucleic acids may be isolated from a biological sample (e.g., nasopharyngeal aspirates, throat swabs, blood fluids, fecal material, etc.). A retrospective diagnosis may be made by serology. Complement Fixation Tests (CFT) are most widely used in this method, although hemagglutination inhibition (HAI) and enzyme immunoassays (EIA) may be used to give a type-specific diagnosis. For more rapid diagnosis, either antigen detection or RNA detection may be performed. Antigen detection may be done by IFT or EIA, however, to achieve the highest level of sensitivity and specificity, RNA detection by reverse transcriptase polymerase chain reaction (RT-PCR) is used. However, the latter is expensive and technically demanding.

Similarly, bacterial detection may be accomplished using a variety of methods, including gram staining, culture, microarray, and polymerase chain reaction (PCR) or real-time PCR. Unlike detection of viruses such as Influenza, which has a genome composed of RNA and therefore requires a transcription step to create target cDNA for use in traditional or real-time PCR, bacterial detection can be accomplished using a standard PCR protocol. Even without the additional RT step, however, PCR or real-time PCR are, as described below, time-consuming and expensive diagnostic methods.

RT-PCR is a laboratory technique used to amplify and quantify a targeted nucleic acid. The procedure follows the general principle of polymerase chain reaction, although in RT-PCR an RNA strand is first reverse transcribed into its DNA complement (cDNA) using the enzyme reverse transcriptase, and the resulting cDNA is amplified using traditional PCR or real-time PCR. The reverse transcription (RT) step can be performed either in the same tube with PCR (one-step PCR) or in a separate one (two-step PCR) using a temperature between about 40° C. and 50° C., depending on the properties of the reverse transcriptase used. The dsDNA is then denaturized at about 95° C., so that the two strands separate and the primers can bind again at lower temperatures and begin a new amplification reaction. DNA extension from the primers takes place using a thermostable Taq DNA polymerase, usually at about 72° C. Real-time RT-PCR provides a method in which the amplicons can be visualized as the amplification progresses using a fluorescent reporter molecule.

Given the high degree of complexity associated with the preparing and processing viral and bacterial nucleic acids from biological samples for detection, diagnosis, and/or quantitation, in cases where rapid diagnosis is sought, there is a need for methods involving fewer steps, fewer technological requirements, and shorter durations.

SUMMARY OF THE INVENTION

The present invention is based on the discovery of a reagent mixture that allows for direct amplification of a sample, without the step of nucleic acid extraction.

In one aspect, the present invention provides a method for identifying the presence or absence of a target nucleic acid from a microorganism in a biological sample obtained from a human, said method comprising: (a) contacting the sample with a DNA polymerase and a buffer under conditions suitable for amplification of the target nucleic acid from the sample without extracting the target nucleic acid from the sample; (b) thermocycling the sample from step (a) such that the target nucleic acid, if present, is amplified; and (c) detecting the amplified target nucleic acid, if present, produced from step (b), wherein the sample nucleic acid is not extracted prior to amplification.

In another aspect, the present invention provides a method for identifying the presence or absence of a target nucleic acid from a microorganism in a biological sample obtained from a human, said method comprising: (a) contacting the sample with a DNA polymerase and a buffer under conditions suitable for amplification of the target nucleic acid from the sample without extracting the target nucleic acid from the sample; (b) thermocycling the sample from step (a) such that the target nucleic acid, if present, is amplified; and (c) detecting the amplified target nucleic acid, if present, produced from step (b), wherein nucleic acid in the sample is not extracted from the sample prior to amplification, and wherein the buffer comprises at least one of component selected from the group consisting of KCl, bovine serum albumin and a surfactant.

In some embodiments, the sample nucleic acid is not diluted prior to step (a). In further embodiments, the sample may be heated prior to step (b), or, in still further embodiments, prior to step (a). The sample may be heated prior to step (b) for at least about 2 minutes at a temperature of at least about 70° C.

In further embodiments, the buffer may comprise potassium chloride (KCl), and, in some embodiments, KCl may be present in a concentration of about 5 mM to about 50 mM. The buffer may further comprise the GOTAQ® Flexi Buffer (Promega, Madison, Wis.), which may be present during step (b) in a 1×-5× concentration. The buffer may also comprise bovine serum albumin. The buffer may comprise a surfactant. In some embodiments, the surfactant is a cationic surfactant. In still further embodiments, the DNA polymerase is a Taq polymerase. The target nucleic acid may be DNA or, in some embodiments, RNA. When the sample is an RNA, it may be further contacted with a reverse transcriptase. The sample may be simultaneously contacted with the DNA polymerase and the reverse transcriptase.

In further embodiments, the sample is selected from the group consisting of blood, serum, plasma, cerebrospinal fluid, oral fluid, and stool. In some embodiments, the sample is whole blood. In some embodiments, the sample is obtained from the buccal region. In still further embodiments, the microorganism may be a virus, or may be selected from the group consisting of an influenza virus, a respiratory syncytial virus, a herpes simplex virus, and an enterovirus. The microorganism may also, in some embodiments, be a bacterium, such as, in further embodiments, C. difficile.

As used herein, the term "RNA" refers to a nucleic acid molecule comprising a ribose sugar as opposed to a deoxyribose sugar as found in DNA. As used herein, RNA refers to all species or RNA including messenger RNA (mRNA), ribosomal RNA (rRNA), transfer RNA (tRNA), as well as small RNA species that have regulatory function. "Small RNA species" have a specific meaning and refer to untranslated RNAs with housekeeping or regulatory roles in bacteria. "Small RNA species" are not rRNA or tRNA.

As used herein, the term "target nucleic acid" refers to any nucleic acid molecule or fragment that is diagnostic of a particular virus or bacteria including, for example, a pathogen virus or bacterial. Target nucleic acids may be DNA or RNA molecules that are derived from the target species.

As used herein, the term "thermocycling" refers to any technique by which a laboratory apparatus is used to amplify segments of nucleic acid with a primer extension reaction using pre-programmed cycles of raised and lowered temperatures. Examples of thermocycling include, but are not limited to, PCR, real-time PCR, and RT-PCR.

As used herein, the term "reverse transcriptase polymerase chain reaction" or "RT-PCR" refers to any technique for synthesizing and amplifying a DNA molecule with a sequence that is a copy of an RNA sequence. RT-PCR is useful in detecting RNA species such as in quantitative analysis of gene expression, as well as for producing DNA copies of RNA for use in cloning, cDNA library construction, probe synthesis, and signal amplification in in situ hybridizations.

As used herein, the term "reagent mix" refers to a composition having all the elements required to perform reverse transcription polymerase chain reaction, or real-time polymerase chain reaction, including but not limited to primers having specificity for the sequence of the diagnostic target RNA or DNA, respectively, and a polymerase.

As used herein, "primer" refers to an oligonucleotide, synthetic or naturally occurring, which is capable of acting as a point of initiation of nucleic acid synthesis or replication along a template strand when placed under conditions in which the synthesis of a complementary strand is catalyzed by a polymerase. Within the context of reverse transcription, primers are composed of nucleic acids and prime on RNA templates. Within the context of PCR, primers are composed of nucleic acids and prime on DNA templates.

As used herein, the term "DNA polymerase" refers to any enzyme that helps catalyze in the polymerization of deoxyribonucleotides into a DNA strand. DNA polymerases act to add free nucleotides to the 3' end of a newly-forming strand, resulting in elongation of the new strand in a 5'-3' direction.

As used herein, "lysis" means perturbation or alteration to a cell wall or viral particle facilitating access to or release of the cellular RNA or DNA. Neither complete disruption nor breakage of the cell wall is an essential requirement for lysis.

As used herein, the term "cycle threshold" or "Ct" refers to the cycle during thermocycling in which the increase in fluorescence due to product formation reaches a significant and detectable level above background signal.

As used herein, the term "direct amplification" refers to a nucleic acid amplification reaction in which the target nucleic acid is amplified from the sample without prior purification, extraction, or concentration. It is a relative measure of the concentration of target in the PCR reaction. Many factors impact the absolute value of Ct besides the concentration of the target. However, artifacts from the reaction mix or instrument that change the fluorescence measurements associated with the Ct calculation will result in template-independent changes to the Ct value.

As used herein, the term "extraction" refers to any action taken to remove nucleic acids from other (non-nucleic acid) material present in the sample. Such action includes, but is not limited to, mechanical or chemical lysis, addition of detergent or protease, or precipitation and removal of non-nucleic acids such as proteins.

As used herein, the term "interfering substance" or "interferent" refers to any substance in a sample that is not a target nucleic acid. Such interfering substances include synthetic and biological substances. Such synthetic substances include chemicals and pharmaceutical drugs. Such biological substances include blood, urine, proteins and other biological molecules.

DETAILED DESCRIPTION

Figure 1A:
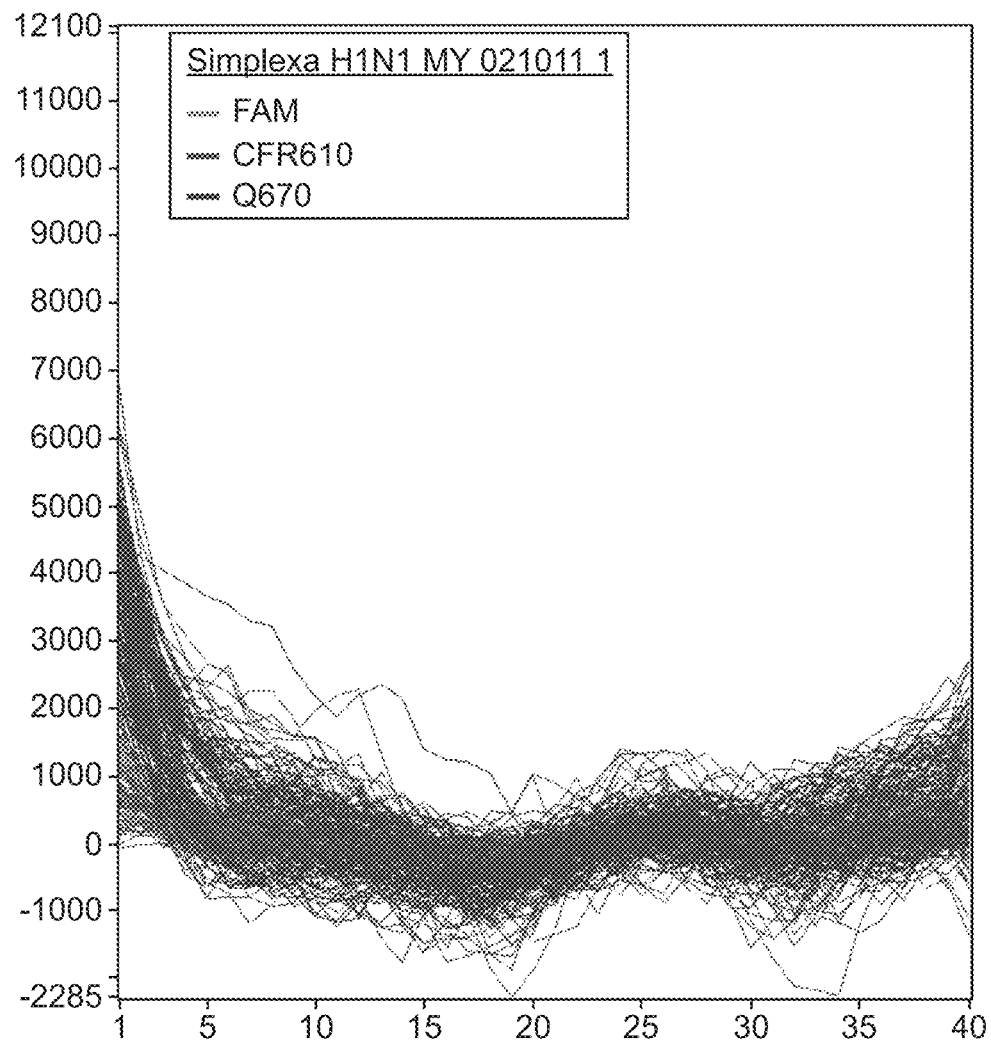
FIG. 1(A) is a line graph depicting the results of an H1N1 assay wherein samples with the FASTSTART® Taq DNA Polymerase buffer (Roche Diagnostics, Indianapolis, Ind.) underwent direct amplification according to the FASTSTART® Taq DNA Polymerase protocol (Roche); (B) is a line graph depicting the results of an H1N1 assay wherein samples with the GOTAQ® DNA polymerase buffer (Promega) underwent direct amplification according to the GOTAQ® DNA polymerase protocol (Promega).
Figure 1B:
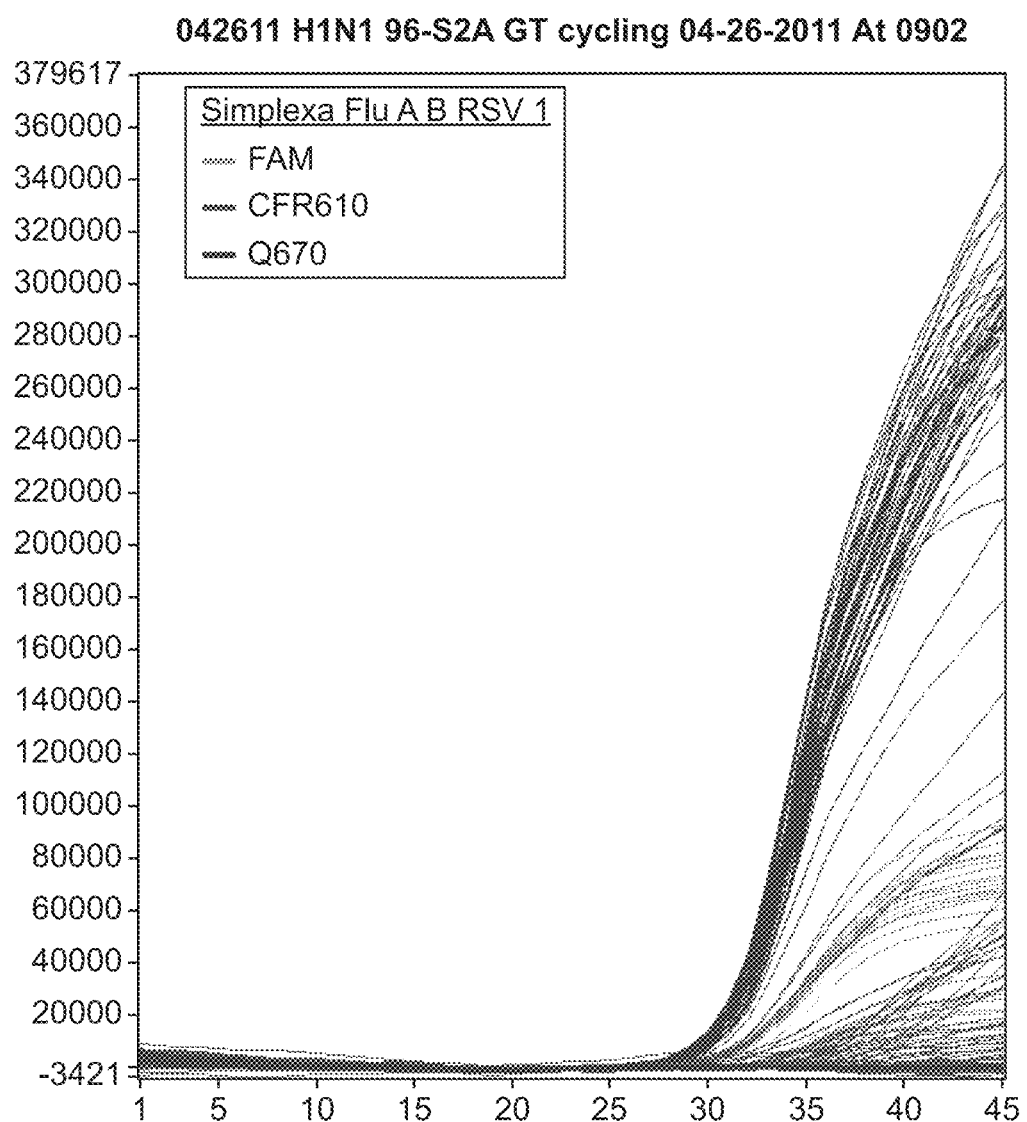

The present invention is directed to diagnostic methods for the detection of human pathogens including, for example, respiratory viruses such as influenza A and B viruses and respiratory syncytial viruses (RSV), enterovirus, herpes simplex virus 1 and 2 (HSV-1 and HSV-2, respectively), varicella zoster virus (VZV); and (pathogenic) bacteria such as *Clostridium difficile* using a PCR method that does not involve an extraction or purification step to isolate viral/bacterial (i.e., target) nucleic acid prior to PCR, and that provides substantially equivalent (or better) sensitivity to similar assays using a specific extraction or purification protocol.

More particularly, the present method involves addition of surfactants to the PCR cocktail to lyse cells or virions, combined certain procedural steps to increase the availability of target nucleic acids. Samples are then heated to about 50° C. prior to the reverse transcriptase step, and this assists with viral lysis and with inactivation of RNAses. Following the RT step, a PCR reaction is performed. For bacterial or DNA virus targets, no reverse transcriptase is required.

Patient samples are added to the reagent mix in a ratio of approximately 10-40% patient sample to 60-90% reagent mix, and, optimally, 20-30% patient sample to 70-80% reagent mix. The reagent mix includes a polymerase derived from *Thermus aquaticus* (e.g., GOTAQ® DNA polymerase; Promega) and an amplification buffer including an ionic detergent (e.g., GOTAQ® Flexi PCR buffer; Promega). The amplification buffer, which may be supplied as a 10× buffer, is diluted to about 5×, about 2.5×, or about 1× concentration for use. The reagent mix further includes KCl (for viral samples only) and $MgCl_2$, as well as dNTPs. In one formulation encompassed by the present invention, the RT-PCR reagent mixture contains of: 0.5 μL 5×GOTAQ® Flexi PCR Buffer (Promega), 0.25 μL 25 mM $MgCl_2$, 0.05 μL 10 mM dNTPs, 0.20 μL 5 U/μL GOTAQ® Flexi DNA polymerase (Promega), and 0.5 μL 10 mM KCl. The patient sample may be heated, either before or after the RT step, and then undergoes PCR.

The reagent mixtures of the present invention allow for the direct amplification of nucleic acids from samples without the requirement for nucleic acid extraction or purification prior to amplification. Without wishing to be bound by any theory, it is believed that, if required, lysis takes place via a combination of heat and surfactant action. Furthermore, it is believed that the inventive reagent mixtures neutralize amplification inhibitors usually present in RT-PCR reactions, obviating the need for dilution of the specimen; a standard technique used in other direct amplification methodologies. The relatively high salt concentrations may contribute to performance by increasing the oligonucleotide binding efficiencies. However, the reagent mixtures vary based on the type of target nucleic acid.

In one embodiment, the reagent mixture for viral RNA detection includes, at a minimum, a reverse transcriptase, high concentrations of forward and reverse primers, optimally scorpion primers, $MgCl_2$, potassium chloride, dNTPs, 5×GOTAQ® Flexi PCR Buffer (Promega; Cat. No. M891A or M890A) or its equivalent, and a *T. aquaticus* derivative polymerase such as 5 U/μl Taq Polymerase (e.g., GOTAQ® Flexi DNA polymerase; Promega Cat. No. M8295). For improved performance, RNAsin may also be added. Additionally, reagent mix for pathogen detection in a spinal fluid or fecal sample also contains BSA.

The reagent mixture for bacterial detection should include, at a minimum, high concentrations of forward and reverse primers, optimally scorpion primers, $MgCl_2$, BSA, dNTPs, 5×GOTAQ® Flexi PCR Buffer (Promega; Cat. No. M891A or M890A) or its equivalent, and a *T. aquaticus* derivative polymerase such as 5 U/μl Taq Polymerase (e.g., GOTAQ® Flexi DNA polymerase; Promega Cat. No. M8295). For improved performance, RNAsin may also be added.

In one embodiment, the assay includes no template control (NTC), positive control, and DNA internal control (IC). The assay can be evaluated based on the Ct values for the controls. In one example, in an assay for detecting *C. difficile*, if the Ct values for NTC is 0 and IC is ≤40, the control is valid. In another example, in an assay for detecting *C. difficile*, if the Ct value for the positive control is 0, the assay is considered invalid. In another example, in an assay for detecting *C. difficile*, if the Ct value for *C. difficile* is ≤40, but ≠0, along with a valid NTC, the assay run is considered valid and acceptable. In another example, in an assay for detecting *C. difficile*, if the Ct value for *C. difficile* is =0, and Ct value for IC is ≤40, but ≠0, *C. difficile* is considered not detected. In another example, in an assay for detecting *C. difficile*, if the Ct value for *C. difficile* is =0, and Ct for IC=0, the assay is considered invalid.

Source of Viral Particles

Obtaining viral nucleic acid for a detection assay from a sample may be by way of collecting a liquid sample, extracting a solid or semi-solid sample, swabbing a surface, or additional technique. Viral RNA may be assayed directly if the existing concentration adequately provides target RNA for an RT-PCR reaction. Alternatively, virions may be concentrated by methods such as centrifugation, binding to a surface through immunoadsorption or other interaction, or filtration.

Source of Bacterial Cells

Obtaining bacterial cells for a detection assay from a sample may be by way of collecting a liquid sample, extracting a solid or semi-solid sample, swabbing a surface, or additional technique. Bacterial cells may be assayed directly if the existing concentration adequately provides target RNA for an RT-PCR reaction. Alternatively, bacterial cells may be concentrated by methods such as centrifugation, binding to a surface through immunoadsorption or other interaction, or filtration. In addition, the bacterial cell number may be increased by growing the cells on culture plates or in liquid medium prior to concentration or direct assay.

Typical bacteria suitable within the context of the invention are gram-negative and gram-positive bacteria including, but not limited to, *Listeria, Escherichia, Salmonella, Campylobacter, Clostridium, Helicobacter, Mycobacterium, Staphylococcus, Camplobacter, Enterococcus, Bacillus, Neisseria, Shigella, Streptococcus, Vibrio, Yersinia, Bordetella, Borrelia*, and *Pseudomonas*.

Target Nucleic Acids

RNA types that may be assayed as target nucleic acids include rRNA, mRNA, transfer-RNA (tRNA), or other RNA polynucleotides. Species of rRNA include 5S, 16S, and 23S polynucleotides, which may contain one or more sub-sequences characteristic of a group of related bacteria. The detection capacity of the characteristic sequence is variable and depends on the level of relatedness of the virus or bacteria to be detected by the assay. Other RNA polynucleotides may be used as diagnostic target RNA so long as they contain unique sub-sequences that adequately distinguish among bacteria at the desired relatedness level. Examples can be identified from tRNA and mRNA species, as well as from any RNA produced in a bacterial cell that includes one or more characteristic sub-sequence. Primers may be designed by one skilled in the art to prime the synthesis of a copy DNA using the target RNA as template in a reverse transcription reaction. One skilled in the art will also know how to design pairs of primers for the amplification of the unique sub-sequences of the target RNA using the copy DNA as template in PCR. It is well known in the art that primers used synchronously in PCR should have similar hybridization melting temperatures. The diagnostic target RNA within the bacterial cell must be made accessible to the RT or RT-PCR reaction composition. After being collected, the nucleic acid sample may be directly added to the reaction composition, which then undergoes thermocycling.

Although optionally present, a specific lysing agent is preferably omitted from the reagent mixture because the sufficient release of viral/bacterial nucleic acids from the sample is obtained without it. Generally, a lysing agent is added prior to contact with the RT, RT-PCR, or PCR reaction composition. The use of lysing agents is well known to those of skill in the art. Lysing agents include but are not limited to chemicals, enzymes, physical shearing, osmotic agents and high temperature. By the term "lysis buffer" is meant a buffer that contains at least one lysing agent. Typical enzymatic lysing agents include, but are not limited to, lysozyme, glucolase, zymolose, lyticase, proteinase K, proteinase E and viral endolysins and exolysins. The viral endolysins and exolysins are from bacteriophages or prophage bacteria and combinations of these. Typical viral endolysins include but are not limited to endolysins from *Listeria* bacteriophages (A118 and PLYI18), endolysins from bacteriophage PM2, endolysins from the *B. subtilis* bacteriophage PBSX, endolysins from *Lactobacillus* prophages Lj928, Lj965 and bacteriophage 15 Phiadh, endolysin (Cpl-I) from the *Streptococcus pneumoniae* bacteriophage Cp-I and the bifunctional peptidoglycan lysin of *Streptococcus agalactiae* bacteriophage B30. These last two have different bacterial strain specificity. Also contemplated are two-component, that is, holin-endolysin, cell 20 lysis genes, holWMY and lysWMY of the *Staphylococcus wameri* M phage varphiWMY Endolysin combinations of these are also contemplated. For a discussion of viral lysis, see especially, Loessner, M J et al. (1995) Applied Environmental Microbiology I 61: 1150-1152.

Rather than using endolysins, treatment with heat prior to or after the RT step aids in lysis in the present method. Incubation of the sample in the range of temperature from about 25° C. to less than about 100° C., and preferably about 50° C. and 75° C., may improve the accessibility of bacterial RNA as a template for RT or RT-PCR. This heat pretreatment may be for a time period in the range of about 1 minute to about 60 minutes, with treatments of 1 to 20 minutes being typical, depending on the temperature of incubation. Heat treatment may include multiple incubations at different temperatures. Heat treatment may be in the presence or absence of RNase inhibitor as described below. Particularly useful treatments are at about 50° C. for about 5 to 20 min in the presence of RNase inhibitor.

At least one RNAse inhibitor may be added to the virions or bacterial cells. Typically, inhibitors and their concentrations are chosen so as not to interfere with any of the primer-directed amplification processes and components. RNase inhibitors are known to those of skill in the art and include chemicals such as guanidinium isothiocyanate and diethyl-pyrocarbonate, protein inhibitors such as Superaseln (Ambion), RNase Block (Stratagene), human placental ribonuclease inhibitor and porcine liver RNase inhibitor (Takara Mirus Bio), anti-nuclease antibodies such as Anti-RNase (Novagen) and Ribonuclease Inhib III (PanVera), and reagents such as RNAlater (Ambion) and RNA protect Bacteria Reagent (Qiagen).

Assay Methods

In the present method, the presence of diagnostic target RNAs is tested by reverse transcription alone or, preferably, by reverse transcription and polymerase chain reaction. When used together, reverse transcription and polymerase chain reaction may be performed sequentially in two steps, or together in one step with all reaction composition reagents being added to the sample. Incubation of the sample in the reverse transcription reaction composition allows a DNA copy from the target RNA to be synthesized. The reagent mix includes a primer that hybridizes to the target RNA to prime the synthesis of the copy DNA. In addition, the reagent mix includes dNTPs, $MgCl_2$, KCl (in viral samples only), a reverse transcriptase and a reverse a transcriptase buffer (in viral samples only), and, for stool samples, BSA (in bacterial samples only). More than one primer may be included if it is desired to make DNA copies from more than one target RNA. However, no RNase inhibitor is used. The product of the reverse transcription reaction may then be transferred to another assay tube where PCR is performed according to protocol well known in the art. The PCR composition typically includes a pair of primers that initiate synthesis of the desired segment of DNA from the reverse transcribed template. In addition, the PCR mix usually comprises dNTPs, a thermostable DNA polymerase such as Taq polymerase, and polymerase buffer. More than one pair of primers may be included if synthesis of multiple segments of DNA is desired. Also a single new primer may be added that will amplify a DNA segment with the original RT-PCR primer as the second primer of the pair. Additional reverse transcriptases that may be used for viral samples include, but are not limited to, HIV Reverse Transcriptase (Ambion), TRANSCRIPTOR™ Reverse Transcriptase (Roche), and THERMOSCRIPT™ Reverse Transcriptase (Invitrogen). Additional DNA polymerases that may be used include, but are not limited to, Pfu, Vent, and SEQUITHERM™ DNA Polymerase (EPICENTRE™).

Regardless of whether the RT-PCR is carried out as two steps or one step, the RT step is run first and typically consists of a single temperature incubation at a temperature of between about 37° C. and about 70° C. Different temperatures are appropriate for different RT enzymes and different primers, as is known to one skilled in the art. The subsequent PCR reaction typically consists of an initial incubation at about 94° C. to about 96° C. for about 6 to about 15 minutes. This step is used to denature the cDNA and also to activate heat activated Taq polymerase enzymes. This is then followed by multiple cycles of amplification of the cDNA target. Three operations are performed during each cycle: target denaturation, primer annealing and primer extension. Target denaturation typically occurs at greater than about 90° C. Primer annealing temperature is dictated by the melting temperature of the specific primers used in the reaction and primer extension is performed at temperatures ranging from about 60° C. to about 72° C. depending on the thermostable polymerase being used. When primer annealing and extension are performed at the same temperature, this is a two temperature PCR compared with a three temperature PCR in which each of the three steps occur at a different temperature. After the amplification phase is complete, a final extension time is typically added to ensure the synthesis of all amplification products.

Target nucleic acids also include DNA including, for example, DNA derived from bacterial species and DNA viruses. Viral DNA suitable for assessment include both DNA obtained directly from the viral capsid as well as DNA integrated into the host genome.

Detection of RT and RT-PCR Product

Methods for directly detecting the cDNA product of an RT reaction are well known to one skilled in the art and make use of labels incorporated into or attached to the cDNA product. Signal generating labels that may be used are well known in the art and include, for example, fluorescent moieties, chemiluminescent moieties, particles, enzymes, radioactive tags, or light emitting moieties or molecules. Fluorescent moieties are particularly useful, especially fluorescent dyes capable of attaching to nucleic acids and emitting a fluorescent signal. A variety of dyes are known in the art such as fluorescein, Texas Red, and rhodamine. Particularly useful are the mono reactive dyes Cy3 and Cy5, both available commercially (from, for example, Amersham Pharmacia Biotech, Arlington Heights, Ill.). A more sensitive way to specifically detect the labeled DNA is to hybridize the products against target DNA sequence molecules that are immobilized in a matrix, such as a nylon membrane or a glass slide. The signals after hybridization can then be scanned with a laser scanner with appropriate filtering to detect the specific dye used. This is well known in the art, especially in DNA microarray technology. A label may be incorporated into the cDNA during its synthesis in the RT reaction, or it may be attached to the cDNA product after its synthesis. For example, the RT reaction can be carried out with labeled primers. One type of labeled primer has attached particles having a large number of signal generating molecules. Reverse transcription using a labeled nucleotide, such as dye-labeled UTP and/or CTP, incorporates a label into the transcribed nucleic acids. Alternatively, a post-synthesis coupling reaction can be used to detect the cDNA products. Attaching labels to nucleic acids is well known to those of skill in the art and may be done by, for example, end-labeling with, e.g. a labeled RNA or by treatment of the nucleic acid with kinase and subsequent attachment of a nucleic acid linker joining the sample nucleic acid to the label, e.g., a fluorophore. In another labeling method, the DNA products from the RT reaction are amplified by coupling to an in vitro transcription reaction. For example, the T7 promoter region is incorporated into the primer used for the RT reaction. A T7 in vitro transcription kit can then be used to generate a large amount of RNA to increase the detection sensitivity. The T7 in vitro transcriptional kit can be purchased from Ambion (2130 Woodward, Austin, Tex.) or other commercial sources.

RT-PCR Detection

Methods for RT-PCR product detection include gel electrophoresis separation and ethidium bromide staining, or detection of an incorporated fluorescent label or radiolabel in the product. Methods that do not require a separation step prior to detection of the amplified product may also be used. These methods are commonly referred to as Real-Time PCR or homogeneous detection. Most real time methods detect amplified product formation by monitoring changes in fluorescence during thermocycling. These methods include but are not limited to: TAQMAN® dual labeled probes (Applied Biosystems, Foster City, Calif. 94404), Molecular Beacons (Tyagi S and Kramer F R (1996) Nat Biotechnol 14:303-308), and SYBR® Green dye (Molecular Probes, Inc Eugene, Oreg. 97402-0469). Some of these same homogeneous methods can be used for end point detection of amplified products as well. An example of this type of method is SYBR® Green dye (Molecular Probes) dissociation curve analysis. In dissociation curve analysis a final slow ramp in temperature, generally about 60° C. to 90° C., combined with fluorescence monitoring can detect the melting point and thereby the presence of an amplified product (Ririe et al. (1997) Anal. Biochem. 245: 154-60).

Assay Sensitivity

The sensitivity of the direct amplification assays can be increased by adding one or more sensitivity-increasing components to the buffer used in the assays. Such components include, but are not limited to, KCl, a surfactant and albumin. In some embodiments, the albumin is bovine serum albumin. In some embodiments, the surfactant is a cationic surfactant. The sensitivity of the direct amplification assays also can be increased by providing additional heating to the assays, such as pre-heating a sample before the reagents are added. In some embodiments, the sensitivity can be increased by a combination of the sensitivity-increasing components and additional heating.

EXAMPLES

The present methods, thus generally described, will be understood more readily by reference to the following examples, which are provided by way of illustration and are not intended to be limiting of the present methods and kits.

Example 1: Universal Master Mix

Except as otherwise noted, the 2.5× Universal Master Mix (UMM) is prepared in the following proportions. The table below provides the volume of reagents suitable to prepare 15 ml of UMM, however, any suitable volume may be prepared according to need.

| Reagent | Volume per 15 ml |
| --- | --- |
| 5X GOTAQ ® Flexi PCR Buffer (Promega; Cat. No. M891A or M890A) | 5.0 ml |
| 25 mM $MgCl_2$ | 2.5 ml |
| 10 mM dNTPs (10 mM for each of dATP, dGTP, dCTP, and dTTP) | 0.5 ml |
| 5 U/µl Taq Polymerase (e.g., GOTAQ ® FlexiDNA Polymerase; Promega Cat. No. M8295) | 2.0 ml |
| 10 mM KCl | 5.0 ml |

The GOTAQ® Flexi PCR buffer (Promega) and equivalents contain ionic detergents and lack magnesium.

Example 2: Effect of KCl on Direct Amplification of Respiratory Virus Nucleic Acids Contrived swab specimens containing influenza B virus were prepared by adding cultured influenza B virus ("Flu B") (Great Lakes strain) to viral transport medium samples, along with an internal control nucleic acid. The Ct values for the Flu B and control nucleic acids were determined in the presence and absence of 25 mM KCl, using the Universal Master Mix of Example 1, with the omission of KCl from the UMM, and further containing either 1 or 2 µl of reverse transcriptase (IMPROM-II™ Reverse Transcriptase, Promega Cat. No. A3800). Serial dilutions of template copies of Flu B virus were assessed at $TCID_{50}$/ml of 158 and 39.5. The RT-PCR reaction was run as follows:

Stage 1: 75° C. for 3 min (once)
Stage 2: 47° C. for 10 min (once)
Stage 3: 97° C. for 2 min (once)
Stage 4: 102° C. for 1 sec. followed by 60° C. for 20 sec. for data collection (repeated 45 times)

The threshold for Ct determination was 50,000. The fluorophores for the Flu B and internal control probes were JOE™ fluorophores (Life Technologies) and Q670, respectively. All assays were run in duplicate and the results averaged.

TABLE 1

Effect of KCl on Direct RT-PCR From Serum (Flu B TCID$_{50}$/ml = 158)

| 25 mM KCl | Reverse Transcriptase | Flu B Ct | Flu B Avg. Ct | Internal Control Ct |
|---|---|---|---|---|
| + | 1 μl | 34.2 | 34.0 | 38.4 |
| + | 1 μl | 33.8 |  | 36.2 |
| + | 2 μl | 33.7 | 33.7 | 37.8 |
| + | 2 μl | 33.7 |  | 38.4 |
| — | 1 μl | 34.0 | 34.4 | 34.6 |
| — | 1 μl | 34.8 |  | 34.6 |
| — | 2 μl | 33.6 | 33.9 | 36.2 |
| — | 2 μl | 34.2 |  | 34.9 |

TABLE 2

Effect of KCl on Direct RT-PCR From Serum (Flu B TCID$_{50}$/ml = 39.5)

| 25 mM KCl | Reverse Transcriptase | Flu B Ct | Flu B Avg. Ct | Internal Control Ct |
|---|---|---|---|---|
| + | 1 μl | 35.9 | 36.3 | 37.6 |
| + | 1 μl | 36.7 |  | 40.2 |
| + | 2 μl | 35.4 | 35.6 | 36.2 |
| + | 2 μl | 35.7 |  | 39.1 |
| — | 1 μl | 35.5 | 37.6 | 41.1 |
| — | 1 μl | 39.6 |  | 35.6 |
| — | 2 μl | 35.7 | 36.1 | 35.8 |
| — | 2 μl | 36.4 |  | 36.3 |

The results in Tables 1 and 2 demonstrate that the presence of KCl enhances the sensitivity of a direct RT-PCR amplification assay for respiratory viruses (Flu B) in serum at low viral concentrations. These results further indicate that the presence of KCl mitigates or negates the necessity for concentrating and/or purifying virus from serum prior to analysis by RT-PCR.

Example 3: Direct Amplification of Respiratory Virus Nucleic Acids from Clinical Samples Various clinical samples (buccal swab and cerebrospinal fluid) were assessed for the presence of HSV-1 and/or HSV-2. The Universal MM from Example 1 was used, with the noted modifications to MgCl$_2$ and KCl.

The buccal swab RT-PCR amplification master mix was:

| Component | Concentration |
|---|---|
| 2.5X Universal MM | 1x |
| Scorpion Forward Primer | 600 nM |
| Reverse Primer | 600 nM |
| MgCl$_2$ | 5 mM |
| Potassium Chloride | 40 mM |

The CSF RT-PCR amplification master mix was:

| Component | Concentration |
|---|---|
| 2.5X Universal MM | 1x |
| Scorpion Forward Primer | 600 nm |
| Reverse Primer | 600 nm |
| MgCl$_2$ | 2.5 mM |
| 100X BSA (10 mg/ml) | 0.1-0.5 mg/ml |
| Potassium Chloride | 40 mM |

Clinical samples were analyzed using both the direct RT-PCR amplification protocol and an RT-PCR amplification protocol that used an initial nucleic acid extraction protocol. Nucleic acids were extracted using a Roche MagNA Pure LC instrument (Roche), and the corresponding Total Nucleic Acid Isolation Kit. A total of 200 μl of sample was extracted, and the nucleic acid was eluted in 50 μl.

For each assay, 10 μl of sample was added to 40 μl of the Master mix described in this Example. The RT-PCR reaction was run as follows:

Stage 1: 75° C. for 3 min (once)
Stage 2: 47° C. for 10 min (once)
Stage 3: 97° C. for 2 min (once)
Stage 4: 102° C. for 1 sec. followed by 60° C. for 10 sec. for data collection (repeated 50 times)

The results are as follows:

TABLE 3

Multiplex Amplification Assessment of Multiple Respiratory Viruses in Clinical Samples

| VBS ID# | Sample Type | Ct Value With Extraction | | Ct Value With Direct Amplification | | |
|---|---|---|---|---|---|---|
| | | HSV-1 | HSV-2 | HSV-1 | HSV-2 | Internal Control |
| 42731 | Swab | N/A | 28.2 | ND | 29.2 | 33.4 |
| 72734 | Swab | N/A | 24.1 | ND | 29.1 | 34.1 |
| 42735 | Swab | N/A | 17.5 | ND | 18.2 | 41.9 |
| 42933 | Swab | 0.0 | 31.5 | ND | 32.8 | 35.0 |
| 42944 | CSF | 0.0 | 0.0 | ND | ND | 35.3 |
| 42946 | CSF | 0.0 | 0.0 | ND | ND | 35.3 |
| 42947 | CSF | 0.0 | 0.0 | ND | ND | 36.2 |
| 041378 | Swab | 20.7 | ND | 20.1 | ND | 33.8 |
| 041379 | Swab | 26.6 | ND | 25.2 | ND | 32.8 |
| 42846 | Swab | 0.0 | 0.0 | ND | ND | 35.0 |
| 42847 | Swab | 0.0 | 0.0 | 42.7 | ND | 34.4 |
| 42848 | Swab | 0.0 | 0.0 | ND | ND | 33.9 |
| 42827 | Swab | 34.2 | 0.0 | 34.4 | ND | 33.2 |
| 42839 | Swab | 0.0 | 33.4 | ND | 35.8 | 34.5 |
| 42952 | CSF | 34.5 | 0.0 | 33.8 | ND | 34.1 |
| 42955 | CSF | 30.2 | 0.0 | 34.6 | ND | 44.6 |
| 42963 | CSF | 32.9 | 0.0 | 34.0 | ND | 35.8 |
| 42984 | CSF | 0.0 | 37.4 | ND | 40.0 | ND |
| 43009 | CSF | 0.0 | 45.2 | ND | 40.5 | 37.7 |
| 42975 | CSF | 0.0 | 37.6 | ND | 39.0 | 38.7 |
| 42995 | CSF | 0.0 | 34.1 | ND | 35.1 | 35.8 |
| 43010 | CSF | 0.0 | 37.9 | ND | 38.4 | 37.9 |
| 43001 | CSF | 0.0 | 32.3 | ND | 33.6 | 37.8 |
| 42957 | CSF | 27.3 | 0.0 | 32.0 | ND | 35.3 |
| 42959 | CSF | 30.1 | 0.0 | 30.1 | ND | 35.1 |
| 42961 | CSF | 31.3 | 0.0 | 32.0 | 43.1 | 34.8 |
| 39929 | Swab | 0.0 | 38.1 | ND | 24.1 | ND |
| 39984 | Swab | 39.8 | 0.0 | 37.6 | ND | 36.3 |
| 39713 | Swab | 38.5 | 0.0 | 30.8 | 43.3 | 36.6 |
| 39724 | Swab | 26.0 | 0.0 | 28.5 | ND | 35.6 |

These data demonstrate that for HSV infected buccal or CSF samples, the direct amplification method described above provides comparable results in a multiplex RT-PCR amplification assay relative to an RT-PCR protocol that performs a nucleic acid extraction and concentration prior at analysis.

Example 4: Effect of the RNAse Inhibitors on Direct Nucleic Acid Amplification Assays A control virus was spiked into viral transport media to create a synthetic sample for analysis using the direct amplification RT-PCR assay described above. For each assay, 10 µl of sample was added to 40 µl of the UMM described in Example 1, in the presence or absence of 1 µl of an RNAse Inhibitor ("RNAsin") (Promega Cat. No. N261B). The RT-PCR reaction was run as follows:
Stage 1: 50° C. for 10 min (once)
Stage 2: 97° C. for 2 min (once)
Stage 3: 102° C. for 1 sec. followed by 58° C. for 20 sec. for data collection (repeated 50 times)

In the absence of the RNAsin, the Ct could not be determined suggesting that the viral RNA was degraded prior to RT. The average Ct in the presence of RNAsin was 32.5 from assays run in duplicate. These results demonstrate that the presence of RNAsin improves the sensitivity of the direct RT-PCR amplification method.

Example 5: Effect of Sample Pre-Heating on Direct Nucleic Acid Amplification Assays Viral transport media was spiked with a combination of influenza A, influenza B, and RSV viruses at approximately 5,000 virus copies/ml to form "FABR" synthetic samples, or with Influenza B virus ($10^{-4}$) alone. These samples were assessed by direct amplification using the Universal Master Mix of Example 1 with the addition of 1 µl Improm II reverse transcriptase and 0.25 µl RNAsin. MS2 phage was added as an internal control. Experimental samples were pre-heated for 3 min at 75° C. and 10 µl of sample was added to 40 µl of Universal Master Mix for each assay. The RT-PCR reaction was run as follows:
Stage 1: 50° C. for 10 min (once)
Stage 2: 97° C. for 2 min (once)
Stage 3: 102° C. for 1 sec. followed by 58° C. for 20 sec. for data collection (repeated 50 times)
The results are as follows:

TABLE 4

Multiplex Amplification Assessment of Multiple Respiratory Viruses in Clinical Samples With Sample Pre-heating

| | Calculated Ct Value | | | |
|---|---|---|---|---|
| | Flu A | Flu B | RSV | Internal Control |
| FABR w/pre-heat | 33.5 | 34.0 | 33.8 | 34.6 |
| Flu B w/pre-heat | ND | 32.3 | ND | 33.8 |
| FABR w/out pre-heat | 33.3 | ND | 37.4 | 33.8 |
| Flu B w/out pre-heat | ND | ND | ND | 33.9 |

Next, control cerebral spinal fluid samples were spiked with HSV-1 virus ($TCID_{50}$/ml=2.14) and control virus were assessed with and without sample pre-heating in the absence of RNAsin. Specificity of the HSV-1 detection methodology was confirmed by simultaneously assessing the samples for the presence of HSV-2 nucleic acid. HSV-2 was not detected in any sample. The results are as follows:

TABLE 5

Direct Amplification Assessment of HSV in Clinical Samples With Sample Pre-heating

| | No Pre-heating | | With Pre-heating | |
|---|---|---|---|---|
| | HSV-1 | I.C. | HSV-1 | I.C. |
| Sample #1 | 38.5 | 31.3 | 36.6 | 29.9 |
| Sample #2 | 38.3 | 31.0 | 35.4 | 29.7 |
| Sample #3 | ND | 30.9 | 35.4 | 29.7 |
| Sample #4 | 39.6 | 31.0 | 35.6 | 29.8 |
| Sample #5 | 41.1 | 31.1 | 36.2 | 29.8 |
| Sample #6 | 38.1 | 30.9 | 35.5 | 29.9 |
| Sample #7 | 37.6 | 31.2 | 35.6 | 29.6 |
| Sample #8 | 40.0 | 31.2 | 35.5 | 29.8 |
| Average | 39.0 | 31.1 | 35.7 | 29.8 |

These results demonstrate that briefly pre-heating the samples prior to direct RT-PCR amplification and assessment enhances the sensitivity of viral detection in most cases (i.e., at least for FluB, RSV, and HSV-1) and does not negatively influence the sensitivity for others (i.e., FluA). Furthermore, sample pre-heating reduces or eliminates the need for the inclusion of an RNAse inhibitor.

Example 6A: Stool Sample Protocol with BSA

A human stool sample is obtained from a patient using standard clinical methodology. Samples are maintained at 2-25° C. for transport and short-term storage and subjected to not more than one freeze/thaw cycle prior to use. For assessment, a flocked swab is dipped into a thoroughly-mixed stool specimen and the excess stools is removed by pressing the swab against the side of the specimen container. The swab is then swirled in 1 ml of Tris-EDTA (TE) buffer and discarded. The sample is heated at 97° C. for 10 minutes. The sample is then diluted 1:4 using the UMM of Example 1 (i.e., 2 µl of sample is added to 8 µl of UMM) with the UMM modifications noted below. Optionally, 2 µl of a solution containing a positive internal control nucleic acid may be added to 8 µl of UMM, which contains 4 µl of the UMM, along with 0.35 mg/ml BSA, 600 nM each of the forward and reverse primers, 300 nM each of internal control primers, and 0.5 µl of internal control DNA). The *C. difficile* target primer was labeled with a FAM™ fluorophores (Life Technologies, Carlsbad, Calif.), and the internal control target was labeled with a Quasar670 fluorophore. Thermocycling began with an initial denaturation step at 97° C. for 2 minutes, followed by 40 cycles of 97° C. for 10 seconds, and 60° C. for 30 seconds. Real-time PCR was performed for 40 cycles and the amplification curves was determined using fluorescently-labeled probes specific for the target nucleic acid, which in this experiment was the *C. difficile* TCD-B gene.

| Component | Concentration |
|---|---|
| 2.5X Universal MM | 1x |
| Scorpion Forward Primer | 600 nM |
| Reverse Primer | 600 nM |
| $MgCl_2$ | 5 mM |
| 100X BSA (10 mg/ml) | 0.35 mg/ml |

Example 6B: Stool Sample Protocol without BSA

In order to determine whether the addition of BSA is likely to decrease inhibition of detection resulting from stool material, the RT-PCR assay was performed according to the protocol used for testing samples with BSA using *Clostridium difficile* DNA as a target both in the presence and absence of BSA. The stool samples were prepared according to the formulation shown in Example 6A, although the BSA-negative samples omitted the 100×BSA. The MagnaPure system (Roche) was used for nucleic acid purification. The PCR reaction was performed as described above, with the BSA-negative PCR formulation plated in wells 1-20, and the BSA-positive PCR formulation was plated in wells 21-40.

The results, which are shown in Table 6, indicate that BSA addition decreases inhibition of gram-positive anaerobic bacterial nucleic acid detection from a stool sample.

TABLE 6

| Well | C. Diff | I.C. |
|---|---|---|
| regular reaction mix | | |
| 1 | 32.8 | 28.2 |
| 2 | 31.2 | 27.7 |
| 3 | 30.4 | 27.4 |
| 4 | 31.3 | 28.2 |
| 5 | 31.0 | 28.1 |
| 6 | 35.5 | 27.3 |
| 7 | 35.8 | 27.4 |
| 8 | 0 | 0 |
| 9 | 36.7 | 27.0 |
| 10 | 36.0 | 27.2 |
| 11 | 30.4 | 27.1 |
| 12 | 30.7 | 27.5 |
| 13 | 0 | 0 |
| 14 | 30.6 | 27.4 |
| 15 | 0 | 0 |
| 16 | 34.5 | 30.7 |
| 17 | 36.8 | 26.8 |
| 18 | 0 | 29.0 |
| 19 | 0 | 27.5 |
| 20 | 31.3 | 27.9 |
| BSA reaction mix | | |
| 21 | 33.3 | 27.7 |
| 22 | 31.4 | 28.1 |
| 23 | 30.5 | 27.7 |
| 24 | 31.2 | 28.0 |
| 25 | 30.8 | 28.4 |
| 26 | 34.6 | 27.1 |
| 27 | 36.4 | 27.4 |
| 28 | 31.3 | 27.7 |
| 29 | 43.1 | 27.2 |
| 30 | 35.6 | 27.1 |
| 31 | 30.8 | 27.3 |
| 32 | 30.6 | 27.5 |
| 33 | 0 | 29.3 |
| 34 | 30.8 | 27.4 |
| 35 | 0 | 30.9 |
| 36 | 34.4 | 29.8 |
| 37 | 35.8 | 27.2 |
| 38 | 40.1 | 27.6 |
| 39 | 0 | 26.7 |
| 40 | 31.4 | 27.8 |

Example 7: Direct RT-PCR Amplification is Buffer-dependent

Samples of Influenza A, and an internal control were assessed using direct amplification to determine whether the enzymes used in the Universal Master Mix as defined in Example 1 are unique in their ability to facilitate a direct detection assay. A hybrid primer concentration was used consisting of 600 nM influenza A scorpion/primer (directed to the matrix gene), 500 nM swine H1 scorpion/primer (directed to the hemagglutinin gene), and 150 nM armored RNA internal control (IC) scorpion primer specific for MS2 phage. The reaction mix was prepared using two distinct enzymes and buffer systems: GO TAQ FLEXI® DNA Polymerase, along with its accompanying 5×PCR Buffer (Promega; Cat. No. M891A or M890A) as a component of universal MM, and FASTSTART® High Fidelity PCR System (Roche), with its accompanying 10× Buffer, as a component of RNA MM, in concentrations as follows:

TABLE 7

Reaction Mix Components and Concentrations

| FASTSTART® | | GOTAQ® | |
|---|---|---|---|
| RNA MM | 4.0 μL | 2.5X universal MM | 4.0 μL |
| Improm II RT | 0.5 μL | Improm II RT | 0.5 μL |
| RNAse inhibitor | 0.2 μL | RNAse inhibitor | 0.2 μL |
| 20X H1N1 primer mix | 0.5 μL | 20X H1N1 primer mix | 0.5 μL |
| 1:100000 MS2 phage | 0.5 μL | 1:100000 MS2 phage | 0.5 μL |
| Water | 2.3 μL | Water | 2.3 μL |
| Sample | 2.0 μL | Sample | 2.0 μL |

The samples consisted of influenza viruses that were spiked into viral transport media. A total of 2 μl of specimen was added to 8 μl of each reaction mix listed above. Each sample was amplified directly without pre-extraction.

Thermocycling was then performed, and amplification curves are determined using fluorescently-labeled probes specific for the target nucleic acids. InfA M gene probes, H1N1-specific HA gene probes, and IC probes were labeled with FAM™ fluorophore (Life Technologies), CFR610, and Q670, respectively. Two cycling protocols were then used for RT-PCR (ICy/Universal 96-well disc; 3M). The GOTAQ® DNA Polymerase (Promega) cycling protocol and the FASTSTART® Taq DNA Polymerase (Roche) cycling protocol assays were first performed with GOTAQ® DNA Polymerase (Promega) cycling protocol, then both were performed with FASTSTART® Taq DNA Polymerase (Roche) cycling protocol. The FASTSTART® Taq DNA Polymerase (Roche) cycling protocol was as follows:
Stage 1: 47° C. for 15 min (once)
Stage 2: 97° C. for 10 min (once)
Stage 3: 97° C. for 15 sec. followed by 60° C. for 30 sec. (repeated 40 times)

The GOTAQ® DNA Polymerase (Promega) cycling protocol was as follows:
Stage 1: 47° C. for 10 min (once)
Stage 2: 97° C. for 2 min (once)
Stage 3: 97° C. for 5 sec. followed by 58° C. for 30 sec. (repeated 40 times)

The results are shown in FIGS. 1(A) and (B) which represent samples with FastStart buffer run using FastStart cycling protocol, and with GOTAQ® DNA Polymerase buffer (Promega) run using GOTAQ® DNA Polymerase (Promega) cycling protocol. No amplification was observed with FASTSTART® Taq DNA Polymerase (Roche) cycling conditions and buffer system, whereas robust amplification was observed using the GOTAQ® DNA Polymerase (Promega) cycling conditions and buffer system.

Figure 2A:
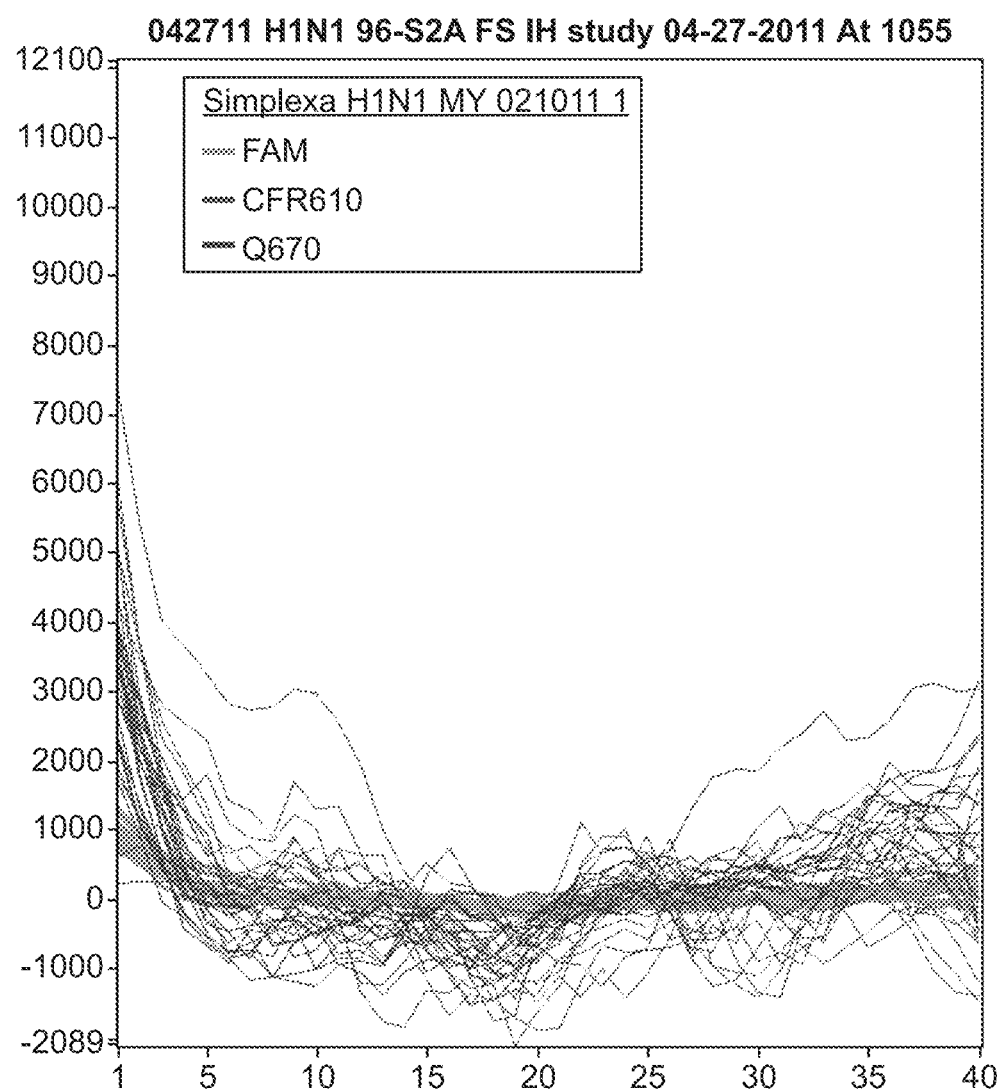
FIGS. 2(A) and (B) are line graphs depicting the effects of two sample storage buffers: universal transport medium (UTM) (A) and 1× Tris-EDTA ("TE") (B) were compared using the FASTSTART® Taq DNA Polymerase protocol (Roche).
Figure 2B:
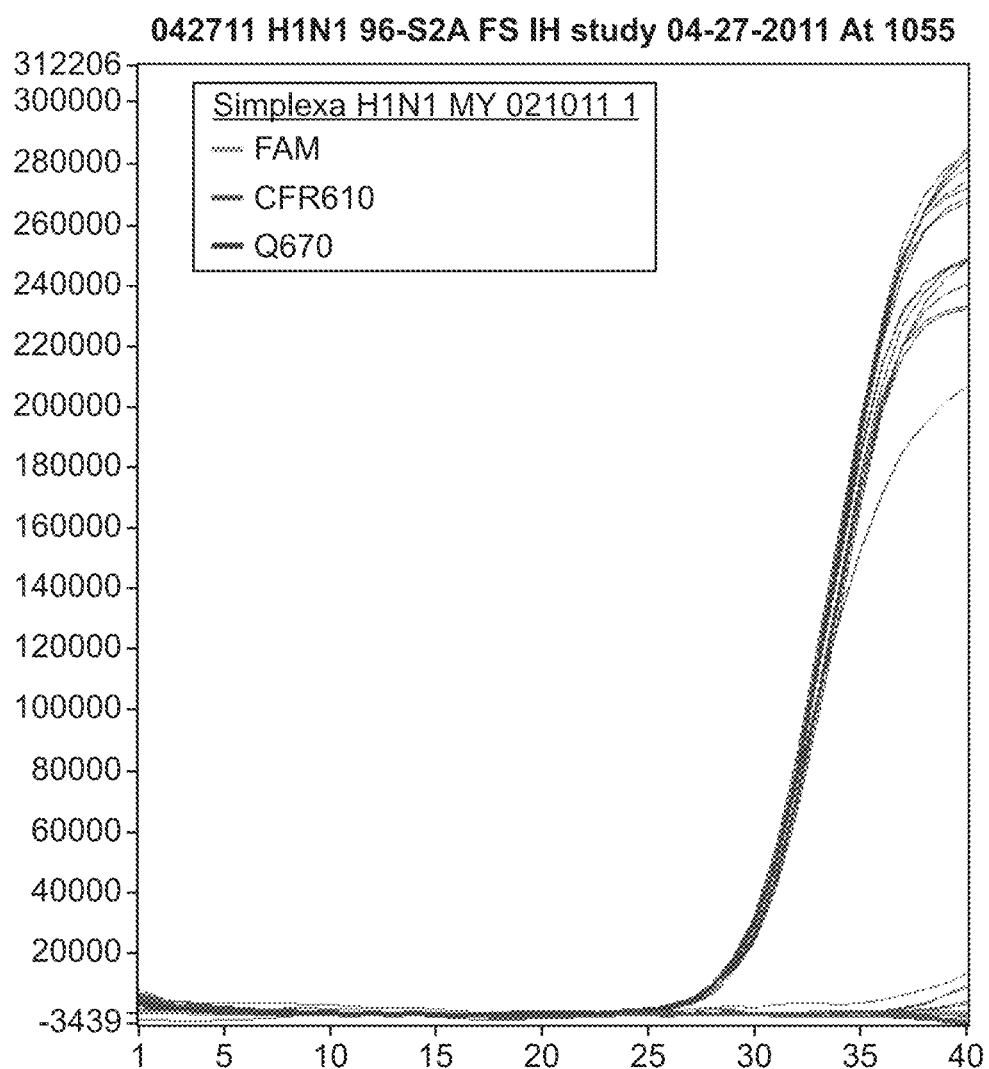

The effect of sample storage buffer was also compared. Specifically, H1N1 nucleic acid amplification from samples stored in universal transport medium (UTM) or 1× Tris-EDTA ("TE") was compared using the FASTSTART® Taq DNA Polymerase protocol (Roche). As shown in FIG. 2, no significant amplification was observed in the UTM samples, whereas the TE samples yielded robust amplification curves.

Figure 3A:
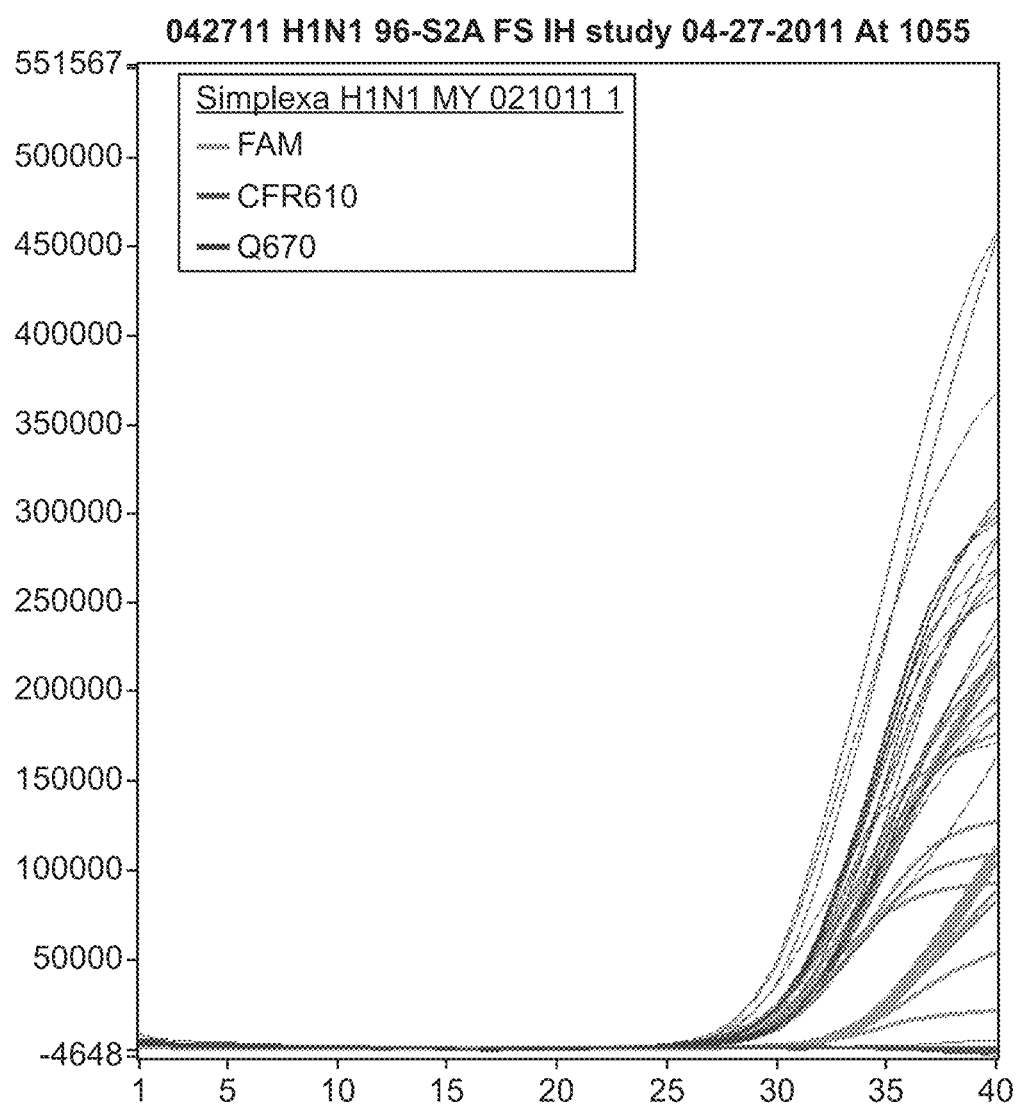
FIG. 3(A) is a line graph depicting the results of an H1N1 assay wherein samples with the FASTSTART® Taq DNA Polymerase buffer (Roche) underwent amplification according to the FASTSTART® Taq DNA Polymerase protocol (Roche) after nucleic acid extraction; (B) is a line graph depicting the results of an H1N1 assay wherein samples with the FASTSTART® Taq DNA Polymerase buffer (Roche) underwent direct amplification according to the Start protocol, without any prior nucleic acid extraction or purification.
Figure 3B:
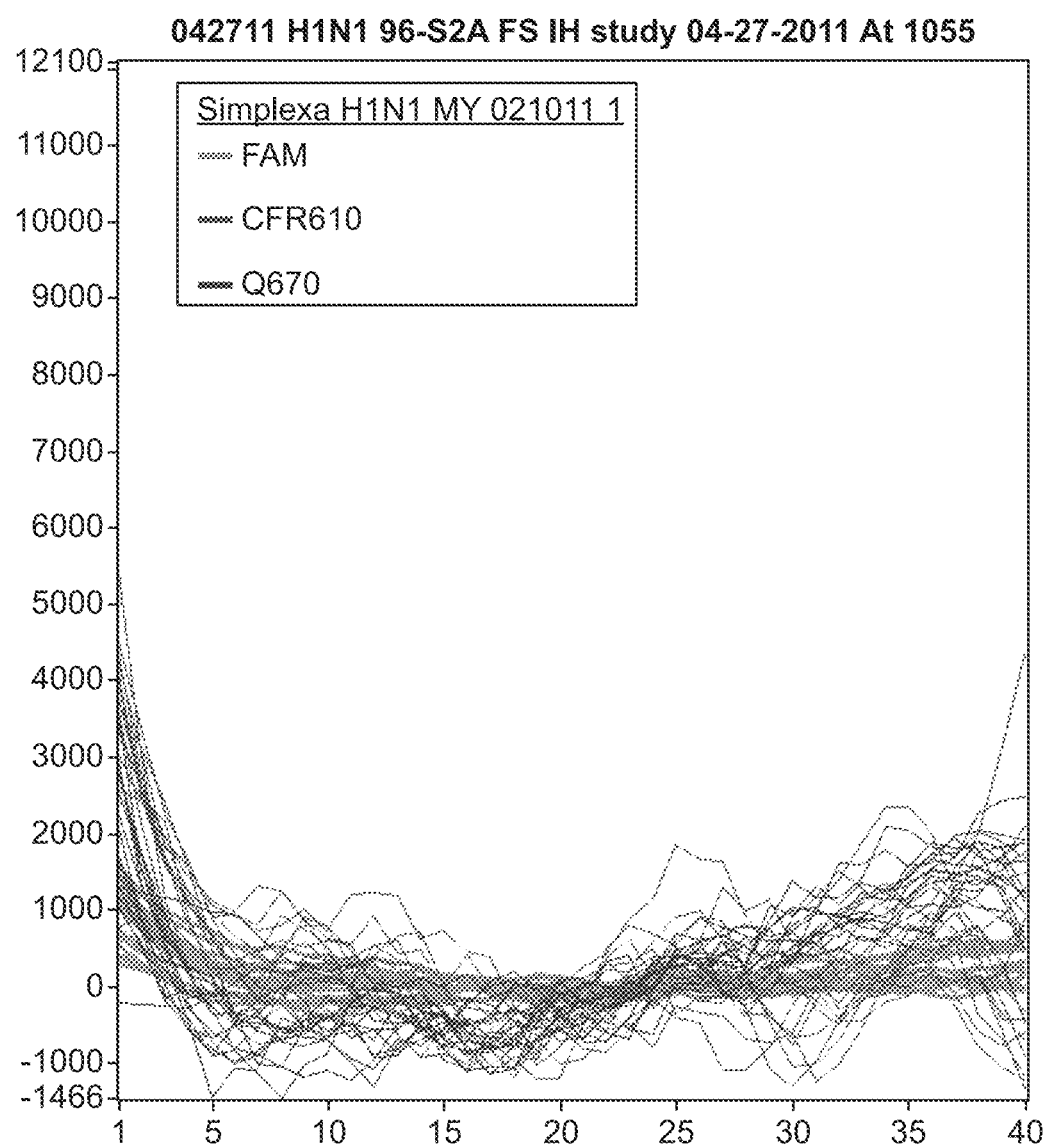

The effect of nucleic acid extraction on the FAST-START® Taq DNA Polymerase (Roche) buffer chemistry and cycling conditions was investigated. As shown in FIG. 3, it was confirmed that the FASTSTART® Taq DNA Polymerase (Roche) protocol failed to amplify H1N1 nucleic acids directly from clinical samples (FIG. 3B). However, robust amplification was observed for samples in which the nucleic acids were extracted prior to the amplification reaction (FIG. 3A). These results demonstrate that not all RT-PCR amplification conditions may be applied to direct amplification/detection systems and that the GOTAQ® DNA Polymerase (Promega) chemistry is particularly suited for this assay format.

The effectiveness of the GOTAQ® DNA Polymerase (Promega) buffer chemistry and cycling conditions for direct amplification was confirmed using Influenza A-positive patient samples (including 2009 pandemic H1N1 positive samples). Amplification was performed using the following parameters:

| PCR Reaction Setup | |
| --- | --- |
| 2.5X universal MM | 4.0 µL |
| Improm II RT | 0.5 µL |
| RNAse inhibitor | 0.2 µL |
| 20X H1N1 primer mix | 0.5 µL |
| 1:100000 MS2 phage | 0.5 µL |
| Water | 2.3 µL |
| Sample | 2.0 µL |

Cycling Conditions
Stage 1: 47° C. for 10 min (once)
Stage 2: 97° C. for 2 min (once)
Stage 3: 97° C. for 5 sec. followed by 58° C. for 30 sec. (repeated 40 times)

Figure 4A:
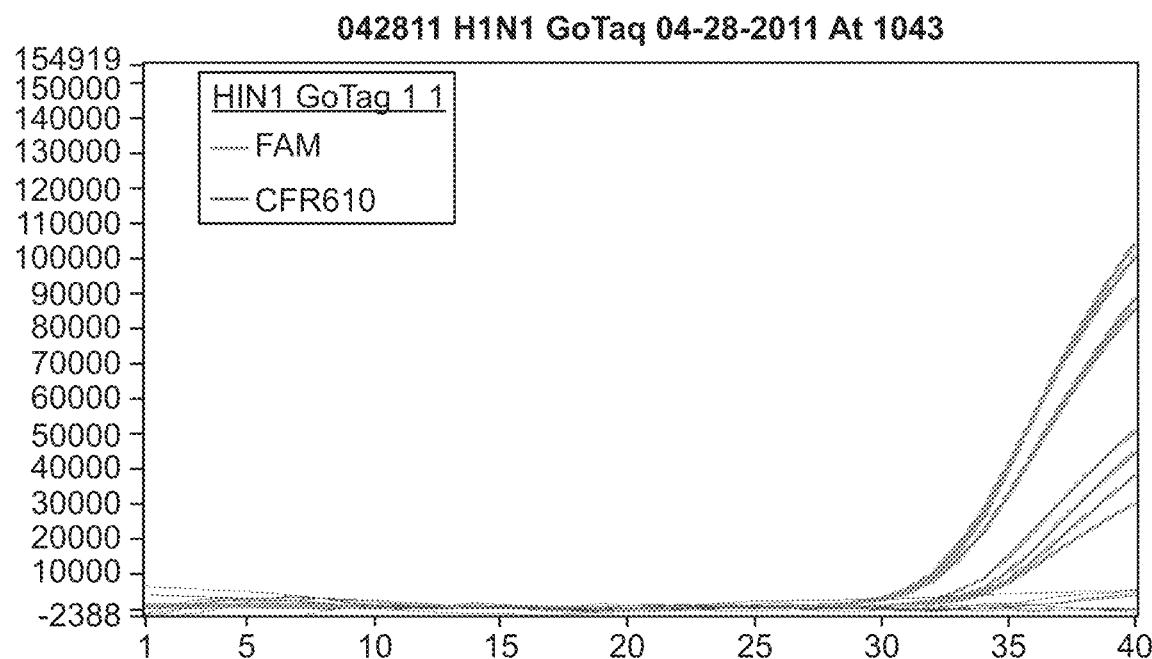
FIGS. 4 (A) and (B) are line graphs demonstrating the effectiveness of the GOTAQ® DNA polymerase (Promega) chemistry and cycling conditions for direct amplification using Influenza A-positive samples.
Figure 4B:
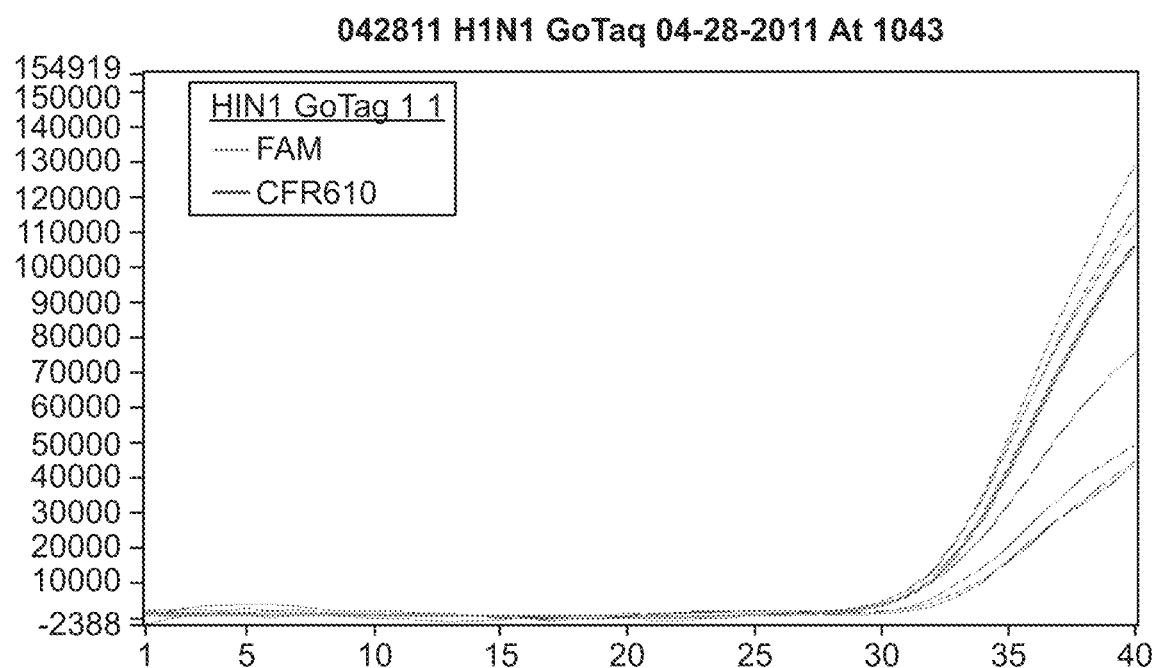

The results shown in FIG. 4A are from samples containing non-pandemic influenza A virus, and amplification of the FAM™ fluorophore (Life Technologies) target indicates detection of influenza A, but not of pandemic H1N1 influenza A. FIG. 4B shows amplification of pandemic H1N1 samples, and demonstrates amplification of the influenza A target, along with the H1N1-specific target.

Example 8: Detection of Flu a, Flu B and RSV by Direct Nucleic Acid Amplification Assays and Comparison with Methods Using Nucleic Acid Extraction Nucleic acid from the clinical specimens (swabs) and control samples were amplified using the direct nucleic acid amplification assays and the results were compared with amplification results using methods involving nucleic acid extraction. The sequences of the amplification primers are shown in the table below.

| Name | Sequence |
| --- | --- |
| Univ Flu A Scorpion | 5' BHQ-1-ACGCTCACCGTGCCCAGTGAGCG-T(FAM)-Spacer 18-GGCATTTTGGACAAAGCGTC TA 3' (SEQ ID NOS: 1-2) |
| Univ Flu A Rev Primer | 5' TCTTGTCACCTCTGACTAAGGGGAT 3' (SEQ ID NO: 3) |
| Flu B Scorpion | 5' JOE-C6-CCGCGG-I-ATTGCAAAGGATGTAATG GAAGTGCCGCGG-BHQ-1-Spacer 18-GAGCTGAATTTCCCAT-I-GAGCT 3' (SEQ ID NOS: 4-5) |
| Flu B Rev Primer | 5' AGCTGCAAAGCAACATTGGAG 3' (SEQ ID NO: 6) |
| RSV A/B Scorpion | 5' CAL Fluor Red 610-ACGCGCTTCACGAAGG CTCCACATACACAGCGCGT-BHQ-2-Spacer 18-TTTTCTAGGACATTGTAYTGAACAG 3' (SEQ ID NOS: 7-8) |
| RSV A/B Rev Primer | 5' GCAAATATGGAAACATACGTGAACAA 3' (SEQ ID NO: 9) |
| RNA IC Scorpion | 5' Quasar 670-ACGCGCTTGGGGCGACAGTCAC GTCGCGCGT-BHQ-2-Spacer 18-CTCGTCGACA ATGGCGGAA 3' (SEQ ID NOS: 10-11) |
| RNA IC Rev Primer | 5' TTCAGCGACCCCGTTAGC 3' (SEQ ID NO: 12) |

Clinical specimens and control samples were heated at 65° C. to 70° C. for 5 min. The reaction mixture was prepared as follows:
Reaction Mixture

| Reaction Component | Volume (µL) |
| --- | --- |
| 2.5X master mix | 4.0 |
| Reverse transcriptase | 0.5 |
| RNase inhibitor | 0.2 |
| 50X flu A primer pair | 0.2 |
| 50X flu B primer pair | 0.2 |
| 50X RSV primer pair | 0.2 |
| 50X internal control primer pair | 0.2 |
| Internal control RNA (heated) | 0.5 |
| Nuclease-free water | 2.0 |
| Reaction Mix | 8.0 |
| Specimen (heated) | 2.0 |
| Total reaction volume | 10.0 |

Thermocycling was then performed using the following cycling parameter.
Cycling Parameters

| Step | Time (sec) | Temp (° C.) | Repeat |
| --- | --- | --- | --- |
| cDNA synthesis | 600 | 47 | 1 |
| Initial heating | 120 | 97 | 1 |
| Denaturation | 5 | 97 | 40 |
| Anneal/extension | 30 | 58 | |

The amplification results using the direct nucleic acid amplification assays were compared with the amplification results obtained using methods involving nucleic acid extraction as shown below.
Clinical Specimens (Swabs) Tested

| Previous result | Number of specimens |
| --- | --- |
| Flu A positive | 35 |
| Flu B positive | 91 |
| RSV positive | 47 |
| Negatives | 19 |
| Total | 193 |

There was 100% concordance between the results obtained using the direct nucleic acid amplification assays and the results obtained using methods involving nucleic acid extraction as shown above.

Example 9: Detection of HSV-1, HSV-2, and VZV by Direct Nucleic Acid Amplification Assays and Comparison with Methods Using Nucleic Acid Extraction Nucleic acids from the clinical specimens as well as contrived samples were amplified using the direct nucleic acid amplification assays and the results were compared with amplification results using methods involving nucleic acid extraction. The reaction mixture was prepared as follows:

Reaction Mixture

| Reaction component | Volume (μL) |
|---|---|
| 2.5X master mix | 4.0 |
| 25X HSV1 primer pair | 0.4 |
| 25X HSV2 primer pair | 0.4 |
| 50X VZV primer pair | 0.2 |
| 50X Internal control primer pair | 0.2 |
| Internal control DNA | 0.2 |
| Nuclease-free Water | 0.6 |
| Reaction mix | 6.0 |
| Sample | 4.0 |
| Total reaction volume | 10.0 |

The sequences of the amplification primers are shown in the table below.

Sequences

```
Sequence Name   Sequence

HSV-1 Scorpion  CFR610-AGCGGCCCGGGTGCCCGGCCAGCCGCT-
                BHQ-2-Spacer 18-GAGGACGAGCTGGCCTTTC
                (SEQ ID NOS: 13-14)

HSV-2 Scorpion  BHQ1-ACGCGCTTCCGGGCGTTCCGCGAGCGCG-T
                (FAM)-Spacer 18-GAGGACGAGCTGGCCTTTC
                (SEQ ID NOS: 15-16)

HSV-1&2 primer  GGTGGTGGACAGGTCGTAGAG
                (SEQ ID NO: 17)

VZV Scorpion    JOE-C6-ACGCGGCTTCTGTTGTTTCGACCGCGT-
                BHQ-1-Spacer 18-CCCCGCTTTAACACATTCCA
                (SEQ ID NO: 18-19)

VZV primer      GCAGTTGCAAACCGGGAT (SEQ ID NO: 20)
```

Thermocycling was performed using the following cycling parameter.

Cycling Parameters

| Step | Time (sec) | Temp (° C.) | Repeat |
|---|---|---|---|
| Initial heating | 120 | 97 | 1 |
| Denaturation | 10 | 97 | 40 |
| Anneal/extension | 30 | 60 | |

The amplification results using the direct nucleic acid amplification assays were compared with the amplification results obtained using methods involving nucleic acid extraction as shown below.

VZV

A total of 32 out of 32 specimens (13 swabs, 2 vitreous fluid, 17 CSF) were detected as positive for VZV using amplification methods involving nucleic acid extraction, while 31 out of 32 specimens detected as positive by the direct amplification method. The CSF sample that was tested negative, was detected with Ct 37.1 when tested with nuclease inhibitor.

HSV-1 and HSV-2

Clinical Specimens (Swabs):

Two HSV-1 samples that were detected as positive using amplification methods involving nucleic acid extraction were also tested as positive using the direct amplification method. Similarly, two HSV-2 samples that were detected as positive using amplification methods involving nucleic acid extraction were also tested as positive using the direct amplification method.

Contrived Samples:

The detection results using the contrived samples in the direct amplification versus an extraction of nucleic acid prior to amplification are shown below for HSV-1 and HSV-2.

HSV-2

| HSV2 ($TCID_{50}$*/mL) | Universal Direct detected/total | Extracted method detected/total |
|---|---|---|
| $2.8 \times 10^3$ | 1/1 | 1/1 |
| $1.4 \times 10^2$ | 1/1 | 1/1 |
| $1.4 \times 10^1$ | 2/2 | 2/2 |
| $1.4 \times 10^0$ | 2/2 | 2/2 |
| $1.4 \times 10^{-1}$ | 2/2 | 2/2 |

*$TCID_{50}$: 50% tissue culture infective dose

HSV-1

| HSV1 ($TCID_{50}$*/mL) | Universal Direct detected/total | Extracted method detected/total |
|---|---|---|
| $1.8 \times 10^3$ | 1/1 | 1/1 |
| $0.9 \times 10^3$ | 2/2 | 2/2 |
| $1.8 \times 10^2$ | 2/2 | 2/2 |
| $0.9 \times 10^2$ | 2/2 | 2/2 |
| $1.8 \times 10^1$ | 1/2 | 2/2 |

*$TCID_{50}$: 50% tissue culture infective dose

Thus, the results using the direct amplification method and the method using nucleic acid extraction are comparable for detecting HSV-1 and HSV-2.

Example 10: Detection of Enterovirus by Direct Nucleic Acid Amplification Assays and Comparison with Methods Using Nucleic Acid Extraction Nucleic acids from the samples were amplified using the direct nucleic acid amplification assays and the results were compared with amplification results using methods involving nucleic acid extraction. The reaction mixture was prepared as follows:

Reaction Mixture

| Reaction Component | Volume (μL) |
|---|---|
| 2.5X master mix | 4.0 |
| Reverse transcriptase | 0.5 |
| RNase inhibitor | 0.1 |

-continued

| Reaction Component | Volume (μL) |
|---|---|
| 50X entero virus primer pair | 0.2 |
| 50X internal control primer pair | 0.2 |
| Internal control RNA | 0.1 |
| Reaction Mix | 5.0 |
| Sample | 5.0 |
| Total reaction volume | 10.0 |

The sequences of the amplification primers are shown in the table below.

Sequences

| Sequence Name | Sequence |
|---|---|
| Enterovirus Scorpion | BHQ1-AGGCCACACGGACACCCAAAGTAGTCGGTGG CC-T(FAM)-Spacer 18-CCCCTGAATGCGGCTA ATC (SEQ ID NOS: 21-22) |
| Enterovirus primer | CAATTGTCACCATAAGCAGCCA (SEQ ID NO: 23) |

Thermocycling was performed using the following cycling parameter.

Cycling Parameters

| Step | Time (sec) | Temp (° C.) | Repeat |
|---|---|---|---|
| cDNA synthesis | 600 | 47 | 1 |
| Initial heating | 120 | 97 | 1 |
| Denaturation | 5 | 97 | 45 |
| Anneal/extension | 30 | 58 | |

The amplification results using the direct nucleic acid amplification assays were compared with the amplification results obtained using methods involving nucleic acid extraction as shown below.

32 samples testing negative by amplification methods involving nucleic acid extraction were also negative by the direct amplification method. 16 samples testing positive by amplification methods involving nucleic acid extraction were also positive by the direct amplification method.

The detection results using the contrived samples in the direct amplification versus an extraction of nucleic acid prior to amplification are shown below.

| Enterovirus (TCID$_{50}$/mL) | Direct Amplification detected/total | Method using Nucleic Acid Extraction method detected/total |
|---|---|---|
| $9.0 \times 10^4$ | 1/1 | 1/1 |
| $9.0 \times 10^3$ | 1/1 | 1/1 |
| $9.0 \times 10^2$ | 2/2 | 2/2 |
| $9.0 \times 10^1$ | 2/2 | 2/2 |
| $9.0 \times 10^0$ | 2/2 | 2/2 |
| $4.5 \times 10^0$ | 4/4 | 4/4 |
| $1.8 \times 10^0$ | 4/4 | 4/4 |

TCID$_{50}$: 50% tissue culture infective dose

Thus, the results using the direct amplification method and the method using nucleic acid extraction are comparable for detecting Enterovirus.

Example 11: Detection of *Clostridium difficile* by Direct Nucleic Acid Amplification Assays and Comparison with Methods Using Nucleic Acid Extraction Nucleic acids from the samples were amplified using the direct nucleic acid amplification assays and the results were compared with amplification results using methods involving nucleic acid extraction.

Stool specimens were obtained from different individuals. Flocked swab was dipped into the stool specimen. Excess stool specimen was removed. The swab was placed in 1 ml of TE buffer, swirled, and the swab was discarded. The samples were heated at 97° for 10 min in a heating block.

The PCR master mix was prepared as follows:

PCR Mix

| Component | Concentration |
|---|---|
| 2.5X Universal MM | 1x |
| Scorpion Forward Primer | 600 nM |
| Reverse Primer | 600 nM |
| MgCl$_2$ | 5 mM |
| 100X BSA (10 mg/ml) | 0.35 mg/ml |

Two microliters of the heated sample was added to eight microliters of the master mix and the PCR was carried out using the following cycling parameters:

| Step | Cycles | Temp (° C.) | Time |
|---|---|---|---|
| 1 | 1 | 97 | 2 min |
| 2 | 40 | 97 | 10 sec |
| | | 60 | 30 sec |

The primers target toxin B region of *C. difficile*. The sequences of the amplification primers and the amplicon are shown below.

C difficile Scorpion primer:
5' d BHQ-1-AGGCAGCTCACCATCAATAATAACTGAACCAGTTGCTGC

C-T(FAM)-Spacer 18-GGTTAGATTTAGATGAAAAGAGATATTATTT

TA 3' (SEQ ID NOS: 24-25)

C difficile Reverse primer:
5' d ACTAATCACTAATTGAGCTGTATCAGGA 3'
(SEQ ID NO: 26)

C. difficile amplicon:
Ggttagatttagatgaaaagagatattattttacagatgaatatattgca gcaactggttcagttattattgatggtgaggagtattattttgatcctga tacagctcaattagtgattagt (SEQ ID NO: 27)

Fluorescent signal from *C. difficile* Scorpion primers was detected at 495 nm and the signal from internal control was detected at 644 nm.

The amplification results using the direct nucleic acid amplification assays were compared with the results obtained using amplification methods involving nucleic acid extraction as shown below.

|  | Methods involving nucleic acid extraction | | | % |
|---|---|---|---|---|
|  | Positive | Negative | Total | Agreement |
| Direct amplification method Positive | 109 | 7 | 116 | 99.1% (109/110) |
| Direct amplification method Negative | 1 | 72 | 73 | 91.1% (72/79) |
| Total | 110 | 79 | 189 |  |

Thus, 99% of the samples identified positive by amplification methods involving nucleic acid extraction were also identified positive by the direct amplification assay, and 91% of the samples identified negative by amplification methods involving nucleic acid extraction also were identified negative by the direct amplification assay.

The Limit of Detection (LoD) was determined using a panel consisting of contrived samples in stool-TE buffer matrix, spiked with *C. difficile* bacterial stock. The panel included negatives (unspiked matrix) and samples of varying concentrations around the approximate LoD (obtained in an earlier phase of testing). Results (positive/negative) of twenty four (24) replicates from three (3) distinct preparations and PCR runs (eight replicates/run) at each level were analyzed with Probit Analysis to determine the lowest concentration which could accurately be detected with 95% probability. The limit of detection is 0.04 cfu/reaction.

Reproducibility of the Assay

Reproducibility study was performed using contrived samples in stool-TE buffer matrix, spiked with *C. difficile* bacterial stock. The panel included a negative (unspiked matrix), a low positive (approximately 2 to 4 times LOD), and a medium positive (approximately 8 to 10 times LOD) samples. The Reproducibility study was performed using two integrated cycler instruments for five days (not consecutive days). Each day, two runs were performed on each instrument. Each run included four replicates of each panel member and positive control (PC) and one replicate of no template control (NTC). The panel and PC were assayed with four replicates, and NTC, in singlicate in each run of the Integrated Cycler instrument. One lot of direct amplification assays was used to run the panel over a period of five days (not consecutive days) at two runs per day per instrument. There was a minimum of two instruments with at least one operator per instrument. The summary of the reproducibility of the results is shown below.

Performance of the Assay in Presence of Potentially Interfering Substances

The performance of this assay was evaluated with potentially interfering substances that may be present in stool samples at the concentrations indicated in the table below. A total of 21 potentially interference substances in replicates of 4 each and baseline (positive) sample in replicates of 5 were tested initially. All but two interference samples tested as "Positive" in all 4 replicates during initial run. All five replicates were "Positive" for two interference substances (Vancomycin & PEPTO BISMOL® bismuth subsalicylate (The Procter & Gamble Company, Cincinnati, Ohio)) upon repeat/confirmatory run. No Interference was observed.

| Substance | Active Ingredient | Final Sample Preparation Concentration | *C. difficile* Result |
|---|---|---|---|
| Mucin | Immunoglobulins, Lysozyme, Polymers, etc | 3 mg/mL | Detected |
| Metronidazole | Metronidazole | 14 mg/mL | Detected |
| Vancomycin | Vancomycin | 1.4 mg/mL | Detected (8 of 9 replicates) |
| Stearic acid | Stearic acid | 4 mg/mL | Detected |
| Palmitic acid | Palmitic acid | 2 mg/mL | Detected |
| Barium sulfate | Barium sulfate | 5 mg/mL | Detected |
| Nystatin | Nystatin | 10,000 USP units/mL | Detected |
| Whole blood | Glucose, Hormones, Enzymes, Ions, Iron, etc. | 5% (v/v) | Detected |
| Antacid and Anti-gas generic (liquid) | Aluminum Hydroxide Magnesium Hydroxide | 0.1 mg/mL | Detected |
| Milk of Magnesia | Magnesium Hydroxide | 0.2 mg/mL | Detected |
| IMODIUM® AD loperamid (Johnson & Johnson, New Brunswick, NJ) | Loperamide | 0.005 mg/mL | Detected |
| PEPTO BISMOL® bismuth subsalicylate (The Procter & Gamble Company, Cincinnati, OH) | Bismuth Subsalicylate | 0.175 mg/mL | Detected (7 of 9 replicates) |
| Moist towelettes generic | Benzalkonium Chloride | 10% (v/v) | Detected |
| antacid generic | Calcium Carbonate | 0.1 mg/mL | Detected |
| Preparation H® ointment (Wyeth, New York, NY) | Phenylephrine | 2% (w/v) | Detected |
| Trojan® spermicide with nonoxynol-9 (Church & Dwight Co., Princeton, NJ) | Nonoxynol-9 | 1.4 mg/mL | Detected |

Quantitative Summary of Reproducibility

| Sample Category | N | Mean | Inter-Instrument | | Inter-Day | | Inter-Run | | Intra-Run | | Total | |
|---|---|---|---|---|---|---|---|---|---|---|---|---|
|  |  |  | SD | % CV | SD | % CV | SD | % CV | SD | % CV | SD | % CV |
| Low Positive | 79* | 35.43 | 0.00 | 0.00 | 0.00 | 0.00 | 0.22 | 0.61 | 0.49 | 1.40 | 0.54 | 1.52 |
| Medium Positive | 79* | 34.13 | 0.00 | 0.00 | 0.00 | 0.00 | 0.16 | 0.48 | 0.48 | 1.39 | 0.50 | 1.48 |
| Positive Control | 80 | 32.80 | 0.00 | 0.00 | 0.00 | 0.00 | 0.07 | 0.20 | 0.59 | 1.80 | 0.59 | 1.81 |
| Negative | 80 | 0.00 |  |  |  |  | Not Applicable | | | | | |
| NTC** | 20 | 0.00 |  |  |  |  | Not Applicable | | | | | |

*One Replicate was "Invalid"
**One Replicate of NTC included in each run

| Substance | Active Ingredient | Final Sample Preparation Concentration | C. difficile Result |
|---|---|---|---|
| 1% Hydrocortisone Cream | Hydrocortisone | 2% (w/v) | Detected |
| FLEET ® mineral oil (C.B. Fleet Company, Lynchburg, VA) | Mineral Oil | 2% (w/v) | Detected |
| Laxative generic | Sennosides | 0.1 mg/mL | Detected |
| ALEVE ® naproxen sodium (Bayer HealthCare, Pittsburgh, PA) | naproxen sodium | 14 mg/mL | Detected |
| K-Y ® Jelly (Johnson & Johnson, New Brunswick, NJ) | water | 2% (w/v) | Detected |

Cross Reactivity

Analytical Specificity for various possible cross reactants was performed. A total of 47 potential cross reactant organisms were tested. Only the Rotavirus organism tested "Negative" in initial testing of all three replicates. Confirmatory run of five replicates for "Rotavirus" also tested "Negative". No cross-reactivity was observed.

| Organism | Suggested source or ID | Concentration tested | Dilution | Result |
|---|---|---|---|---|
| Acinetobacter baumannii | ATCC 19606 | 0.5 McFarland | 1:1 | Did not cross react |
| Acinetobacter lwoffii | ATCC 15309 | 0.5 McFarland | 1:1 | Did not cross react |
| Adenovirus 40 | ATCC VR-931 | N/A | $1:10^5$ | Did not cross react |
| Bacillus cereus | ATCC 10702 | $10^6$ CFU/mL | 1:860 | Did not cross react |
| Bacteroides merdae | ATCC 43184 | 0.5 McFarland | Neat | Did not cross react |
| Bacteroides stercoris | ATCC 43183 | 0.5 McFarland | Neat | Did not cross react |
| Bifidobacterium adolescentis | ATCC 15703 | 0.5 McFarland | Neat | Did not cross react |
| Campylobacter coli | ATCC 43479 | 0.5 McFarland | 1:1 | Did not cross react |
| Campylobacter jejuni sub sp jejuni | ATCC 33292 | 0.5 McFarland | 1:1 | Did not cross react |
| Candida albicans | ZeptoMetrix 0801504 | $10^6$ CFU/mL | 1:100 | Did not cross react |
| Clostridium tetani | ATCC 19406 | 0.5 McFarland | Neat | Did not cross react |
| Citrobacter freundii | ZeptoMetrix 0801563 | $10^6$ CFU/mL | 1:5200 | Did not cross react |
| Citrobacter koseri | ATCC 27028 | 0.5 McFarland | 1:1 | Did not cross react |
| Clostridium butyricum | ATCC 12398 | 0.5 McFarland | Neat | Did not cross react |
| Clostridium difficile | (non-toxigenic ATCC 700057) | 0.5 McFarland | 1:4500 | Did not cross react |
| Clostridium innocuum | ATCC 14501 | 0.5 McFarland | Neat | Did not cross react |
| Clostridium novyi | ATCC 19402 | 0.5 McFarland | Neat | Did not cross react |
| Clostridium paraputrificum | ATCC 25780 | 0.5 McFarland | Neat | Did not cross react |
| Clostridium perfringens | ATCC 13124 | 0.5 McFarland | Neat | Did not cross react |
| Clostridium septicum | ATCC 12464 | 0.5 McFarland | Neat | Did not cross react |
| Clostridium symbiosum | ATCC 14940 | 0.5 McFarland | Neat | Did not cross react |
| Coxsackie virus | ATCC VR-30 | $10^5$ TCID$_{50}$/mL | 1:28.1 | Did not cross react |
| Cytomegalovirus AD169 | ZeptoMetrix 0810003CF | $10^5$ TCID$_{50}$/mL | 1:20.8 | Did not cross react |
| Echovirus | ATCC VR-36 | $10^5$ TCID$_{50}$/mL | 1:15.8 | Did not cross react |
| Enterobacter aerogenes | ZeptoMetrix 0801518 | $10^6$ CFU/mL | 1:10000 | Did not cross react |
| Enterobacter cloacae | ATCC 13047 | 0.5 McFarland | 1:1 | Did not cross react |
| Enterococcus faecalis | ATCC 51299 | 0.5 McFarland | 1:1 | Did not cross react |
| Escherichia coli | ZeptoMetrix 0801517 | $10^6$ CFU/mL | 1:20000 | Did not cross react |
| Fusobacterium varium | ATCC 8501 | 0.5 McFarland | Neat | Did not cross react |
| Klebsiella oxytoca | ATCC 33496 | 0.5 McFarland | 1:1 | Did not cross react |
| Lactobacillus acidophilus | ZeptoMetrix 0801540 | $10^6$ CFU/mL | 1:2120 | Did not cross react |
| Lactobacillus reuteri | ATCC 23272 | 0.5 McFarland | Neat | Did not cross react |
| Listeria monocytogenes | ZeptoMetrix 0801534 | $10^6$ CFU/mL | 1:11800 | Did not cross react |
| Norovirus | Clinical sample | N/A | Swab | Did not cross react |
| Peptostreptococcus anaerobius | ATCC 27337 | 0.5 McFarland | Neat | Did not cross react |
| Proteus mirabilis | ZeptoMetrix 0801544 | $10^6$ CFU/mL | 1:144 | Did not cross react |
| Pseudomonas aeruginosa | ZeptoMetrix 0801519 | $10^6$ CFU/mL | 1:10500 | Did not cross react |
| Rotavirus | Clinical sample | N/A | Swab | Did not cross react |
| Rotavirus (retest) | ZeptoMetrix 0810041CF | $10^5$ TCID$_{50}$/mL | 1:200 | Cross reacted* |
| Salmonella enterica subsp. Enterica (formerly Salmonella choleraesuis subsp. choleraesuis) | ATCC 14028 | 0.5 McFarland | 1:1 | Did not cross react |
| Salmonella enterica subsp. arizonae (Borman) Le Minor et al. deposited as Arizona arizonae Kauffmann and Edwards | ATCC 13314 | 0.5 McFarland | 1:1 | Did not cross react |
| Serratia marcescens | ATCC 13880 | 0.5 McFarland | 1:1 | Did not cross react |
| Shigella boydii | ATCC 9207 | 0.5 McFarland | 1:1 | Did not cross react |
| Shigella dysenteriae | ATCC 11835 | 0.5 McFarland | 1:1 | Did not cross react |
| Shigella sonnei | ATCC 29930 | 0.5 McFarland | 1:1 | Did not cross react |

| Organism | Suggested source or ID | Concentration tested | Dilution | Result |
|---|---|---|---|---|
| *Streptococcus agalactiae* | ZeptoMetrix 0801545 | $10^6$ CFU/mL | 1:22000 | Did not cross react |
| *Vibrio cholerae* | Genomic DNA | 5 ng/µL | N/A | Did not cross react |
| Negative stool | NA-negative matrix | NA-negative matrix | N/A | Did not cross react |

*Subsequent testing of the sample at a clinical testing lab confirmed the sample was positive for *C. difficile*.

Example 12: Detection of Group a *Streptococcus* by Direct Nucleic Acid Amplification Assays and Comparison with Methods Using Nucleic Acid Extraction Nucleic acids from the samples were amplified using the direct nucleic acid amplification assays and the results were compared with amplification results using methods involving nucleic acid extraction.

Swab samples were used in the direct amplification assay. The PCR master mix was prepared as follows:

PCR Mix

| Component | Concentration |
|---|---|
| 2.5X Universal MM | 1x |
| Scorpion Forward Primer | 600 nM |
| Reverse Primer | 600 nM |
| $MgCl_2$ | 2.5 mM |
| Potassium Chloride | 40 mM |

2 uL of transport medium from a swab sample was added to 8 uL of PCR master mix and PCR was carried out using the following cycling parameters:

| Step | Cycles | Temp (° C.) | Time |
|---|---|---|---|
| 1 | 1 | 97 | 6 min |
| 2 | 40 | 97 | 10 sec |
|   |   | 60 | 30 sec |

The sequences of the amplification primers and the amplicon are shown below. Group A *Streptococcus* Scorpion primer:

```
Group A Streptococcus Scorpion primer:
5' d BHQ-1-AGCGGCACTCCAAAAATCAGCAGCTATCAAAGCAGGT GTGCCGC-T(FAM)-Spacer 18-AAGCTTAATATCTTCTGCGCTTC

GT 3' (SEQ ID NOS: 28-29)

Group A Streptococcus Reverse primer:
5' d TAACCCAGTATTTGCCGATCAA 3' (SEQ ID NO: 30)

Group A Streptococcus amplicon:
taacccagtatttgccgatcaaaactttgctcgtaacgaaaaagaagc aaaagatagcgctatcacatttatccaaaaatcagcagctatcaaagc aggtgcacgaagcgcagaagatattaagctt (SEQ ID NO: 31)
```

The amplification results using the direct nucleic acid amplification assays were compared with the results obtained using amplification methods involving nucleic acid extraction as shown below.

| | | Methods involving nucleic acid extraction | | | % |
|---|---|---|---|---|---|
| | | Positive | Negative | Total | Agreement |
| Direct amplification method | Positive | 45 | 3 | 48 | 93.8% (45/48) |
| | Negative | 3 | 349 | 352 | 99.1% (349/352) |
| Total | | 48 | 352 | 400 | |

Thus, 93.8% of the samples identified positive by amplification methods involving nucleic acid extraction also were identified positive by the direct amplification assay, and 99% of the samples identified negative by amplification methods involving nucleic acid extraction also were identified negative by the direct amplification assay.

Example 13: Detection of Flu a, Flu B and RSV by Direct Nucleic Acid Amplification Assays in the Presence of Interfering Substances Using the experimental protocol of Example 8, nucleic acid from clinical specimens were amplified using the direct nucleic acid amplification assays in the presence of various interfering substances listed in the table below:

| Interferent ID | Interferent | Concentration tested |
|---|---|---|
| Control | None | N/A |
| 1 | human blood | 2% (v/v) |
| 2 | AFRIN ® nasal spray (Oxymetazoline) (Schering, Kenilworth, NJ) | 15% (v/v) |
| 3 | BECONASE AQ ® (Beclomethasone) (Glaxo, United Kingdom) | 5% (v/v) |
| 4 | Nasal corticosteroid (Fluticasone) | 5% (v/v) |
| 5 | Nasal gel (ZICAM ® nasal gel) (Zicam, Scottdale, AZ) | 5% (v/v) |
| 6 | Mucin | 60 µg/mL |
| 7 | Systemic antibacterial (Tobramycin) | 10 µg/mL |
| 8 | RELENZA ® (Zanamivir) (Glaxo, United Kingdom) | 3.3 mg/mL |
| 9 | TAMIFLU ® oseltamivir phosphate (Oseltamivir) (Hoffmann-La Roche, Nutley, NJ) | 1.0 µM |
| 10 | Topical antibiotic (Mupirocin) | 2.5 mg/mL |

The direct amplification assays were conducted in duplicates for each potential interfering substance. The Q670 fluorescent label used for an internal control, PC represents a positive control and NEG represents a negative control.

The table below presents Ct results of detecting the Flu A virus in the presence of the potential interfering substances.

| Interferent | FAM™ fluorophore | JOE™ fluorophore | CFR610 | Q670 |
|---|---|---|---|---|
| Control | 34.8 | 0 | 0 | 33.5 |
| Control | 34.3 | 0 | 0 | 33.3 |
| 1 | 35.2 | 0 | 0 | 33.4 |
| 1 | 35.4 | 0 | 0 | 33.4 |
| 2 | 35.2 | 0 | 0 | 32.3 |
| 2 | 35.0 | 0 | 0 | 32.4 |
| 3 | 34.5 | 0 | 0 | 33.1 |
| 3 | 34.4 | 0 | 0 | 33.1 |
| 4 | 34.4 | 0 | 0 | 33.2 |
| 4 | 34.3 | 0 | 0 | 33.2 |
| 5 | 35.6 | 0 | 0 | 33.0 |
| 5 | 34.8 | 0 | 0 | 32.4 |
| 6 | 35.2 | 0 | 0 | 32.8 |
| 6 | 35.2 | 0 | 0 | 33.2 |
| 7 | 35.7 | 0 | 0 | 33.2 |
| 7 | 34.6 | 0 | 0 | 33.3 |
| 8 | 35.0 | 0 | 0 | 33.5 |
| 8 | 35.1 | 0 | 0 | 33.5 |
| 9 | 35.2 | 0 | 0 | 33.2 |
| 9 | 34.5 | 0 | 0 | 33.5 |
| 10 | 35.1 | 0 | 0 | 33.3 |
| 10 | 34.8 | 0 | 0 | 33.3 |
| Avg Ct | 34.9 | 0.0 | 0.0 | 33.1 |
| PC | 36.0 | 33.2 | 34.4 | 32.8 |
| NEG | 0 | 0 | 0 | 33.4 |

The table below presents Ct results of detecting the Flu B virus in the presence of the potential interfering substances.

| Name | FAM™ fluorophore | JOE™ fluorophore | CFR610 | Q670 |
|---|---|---|---|---|
| Control | 0 | 34.7 | 0 | 33.5 |
| Control | 0 | 34.3 | 0 | 33.4 |
| 1 | 0 | 34.9 | 0 | 33.4 |
| 1 | 0 | 34.7 | 0 | 33.6 |
| 2 | 0 | 35.1 | 0 | 32.6 |
| 2 | 0 | 34.2 | 0 | 32.7 |
| 3 | 0 | 34.6 | 0 | 32.7 |
| 3 | 0 | 34.2 | 0 | 32.7 |
| 4 | 0 | 34.8 | 0 | 33.0 |
| 4 | 0 | 34.9 | 0 | 32.8 |
| 5 | 0 | 34.5 | 0 | 33.4 |
| 5 | 0 | 34.4 | 0 | 33.2 |
| 6 | 0 | 34.4 | 0 | 33.2 |
| 6 | 0 | 34.4 | 0 | 33.1 |
| 7 | 0 | 35.2 | 0 | 33.1 |
| 7 | 0 | 34.3 | 0 | 33.6 |
| 8 | 0 | 35.0 | 0 | 34.1 |
| 8 | 0 | 34.4 | 0 | 34.0 |
| 9 | 0 | 34.9 | 0 | 33.3 |
| 9 | 0 | 34.3 | 0 | 33.4 |
| 10 | 0 | 34.4 | 0 | 33.4 |
| 10 | 0 | 34.3 | 0 | 33.3 |
| Avg Ct | 0.0 | 34.6 | 0.0 | 33.3 |
| PC | 35.4 | 33.4 | 34.5 | 32.7 |
| NEG | 0 | 0 | 0 | 32.7 |

The table below presents Ct results of detecting the RSV virus in the presence of the potential interfering substances.

| Name | FAM™ fluorophore | JOE™ fluorophore | CFR610 | Q670 |
|---|---|---|---|---|
| Control | 0 | 0 | 34.9 | 32.6 |
| Control | 0 | 0 | 31.4 | 33.1 |
| 1 | 0 | 0 | 34.4 | 33.6 |
| 1 | 0 | 0 | 34.5 | 33.2 |
| 2 | 0 | 0 | 34.9 | 32.6 |
| 2 | 0 | 0 | 34.9 | 32.2 |
| 3 | 0 | 0 | 34.9 | 32.4 |
| 3 | 0 | 0 | 34.8 | 33.3 |
| 4 | 0 | 0 | 35.1 | 33.5 |
| 4 | 0 | 0 | 31.0 | 34.0 |
| 5 | 0 | 0 | 34.7 | 33.3 |
| 5 | 0 | 0 | 34.1 | 33.5 |
| 6 | 0 | 0 | 35.1 | 33.0 |
| 6 | 0 | 0 | 34.8 | 33.4 |
| 7 | 0 | 0 | 35.4 | 33.9 |
| 7 | 0 | 0 | 34.8 | 34.1 |
| 8 | 0 | 0 | 34.9 | 33.3 |
| 8 | 0 | 0 | 35.2 | 33.6 |
| 9 | 0 | 0 | 34.5 | 33.8 |
| 9 | 0 | 0 | 35.1 | 33.5 |
| 10 | 38.5* | 0 | 35.1 | 33.6 |
| 10 | 0 | 0 | 34.7 | 34.0 |
| Avg Ct | N/A | 0.0 | 34.5 | 33.3 |
| PC | 33.3 | 33.0 | 32.7 | 33.2 |
| NEG | 0 | 0 | 0 | 33.0 |

*False-positive FAM™ fluorophore (Life Technologies) signal was detected in 1 of 2 replicates.

The results were verified to be accurate based on a lack of valid amplification signal in the FAM™ fluorophores (Life Technologies), JOE™ fluorophore (Life Technologies) or CFR610 channels for the negative control and a Ct<40 in the Q670 channel. Also, the PC reactions gave a Ct<40 in the FAM™ fluorophores (Life Technologies), JOE™ fluorophore (Life Technologies) and CFR610 channels.

The results of the direct amplification assays for detecting Flu A, Flu B and RSV demonstrate that there was no significant change in Ct values with any of the interferents for any of the viruses tested, as compared with the control samples without any interfering substance. The direct amplification assays are therefore not affected by potential interfering substances when detecting low positive samples of these viruses.

Example 14: Detection of HSV-1 and HSV-2 by Direct Nucleic Acid Amplification Assays in the Presence of Interfering Substances Using the experimental protocol of Example 3, nucleic acid on a negative swab matrix and in synthetic cerebral-spinal fluid were amplified using the direct nucleic acid amplification assays in the presence of various interfering substances listed in the table below:

| Interferent ID | Interfering Substance | Matrix | Concentration tested |
|---|---|---|---|
| 1 | Whole Blood | swab and CSF | 10% (v/v) |
| 2 | Female Urine | swab | 10% (v/v) |
| 3 | Albumin (protein) | swab and CSF | 10 mg/mL |
| 4 | Casein (protein) | swab and CSF | 10 mg/mL |
| 5 | K-Y ® Jelly Johnson & Johnson, New Brunswick, NJ) | swab | 5% (v/v) |
| 6 | Acyclovir (Acycloguanosine) | swab and CSF | 2.5 mg/mL |
| 7 | BETADINE ® microbicide (topical antiseptic) (Purdue Products, Stamford, CT) | swab and CSF | 5% (v/v) |
| 8 | White Blood Cell | CSF | 5.5 × 10e8 WBC/mL |
| 9 | Hemoglobin* | CSF | 0.625-5.0 mg/mL |
| Control | None | swab and CSF | N/A |

The whole blood potential interfering substance (Interferent ID: 1) was tested at 10%, which is clinically more relevant than purified hemoglobin. Also, the hemoglobin potential interfering substance (Interferent ID: 9) was tested at higher concentrations of 5.0-1.25 mg/mL, but detection of HSV-1 and HSV-2 were inhibited at these concentrations.

The direct amplification assays were conducted in triplicates for each potential interfering substance. The Q670 fluorescent label was used for an internal control, PC represents a positive control and NEG represents a negative control.

The table below presents Ct results of detecting the HSV-1 virus on the negative swab matrix in the presence of the potential interfering substances.

| Interferent ID | HSV-2 (FAM ™) | HSV-1 (CFR610) | IC (Q670) |
|---|---|---|---|
| Control | 0 | 33.7 | 32.7 |
| Control | 0 | 33.1 | 32.3 |
| Control | 0 | 32.9 | 32.2 |
| Control | 0 | 35.8 | 32.2 |
| 1 | 0 | 32.1 | 31.7 |
| 1 | 0 | 33.1 | 31.5 |
| 1 | 0 | 31.8 | 31.9 |
| 2* | 0 | 30.9 | 31.1 |
| 2* | 0 | 30.8 | 31.0 |
| 2* | 0 | 30.4 | 30.9 |
| 3 | 0 | 34.1 | 31.0 |
| 3 | 0 | 31.7 | 31.2 |
| 3 | 0 | 32.4 | 31.4 |
| 4 | 0 | 32.1 | 31.7 |
| 4 | 0 | 32.5 | 31.1 |
| 4 | 0 | 32.1 | 31.5 |
| 5 | 0 | 31.7 | 31.2 |
| 5 | 0 | 31.2 | 31.6 |
| 5 | 0 | 31.7 | 31.6 |
| 6 | 0 | 31.5 | 31.1 |
| 6 | 0 | 34.2 | 31.0 |
| 6 | 0 | 32.7 | 31.3 |
| 7 | 0 | 36.1 | 31.5 |
| 7 | 0 | 33.4 | 31.7 |
| 7 | 0 | 33.6 | 32.1 |
| PC (day 1) | 31.0 | 31.2 | 31.0 |
| NEG (day 1) | 0 | 0 | 31.1 |
| PC (day 2) | 30.5 | 31.2 | 31.0 |
| NEG (day 2) | 0 | 0 | 31.1 |

The fluid check for female urine (Interferent ID: 2) failed, as indicated by higher fluorescent values than the control with no sample, although HSV-1 was detected in the female urine samples. The K-Y brand jelly (Interferent ID: 5) produced an earlier Ct value compared to control samples, even though the same HSV-1 levels were used for all potential interference substance testing. The female urine and K-Y jelly potential interferents were retested and reproducibly produced an earlier Ct for both samples.

The table below presents Ct results of detecting the HSV-2 virus on the negative swab matrix in the presence of the potential interfering substances.

| Interferent ID | HSV-2 (FAM ™) | HSV-1 (CFR610) | IC (Q670) |
|---|---|---|---|
| Control | 33.5 | 0 | 31.6 |
| Control | 33.2 | 0 | 31.7 |
| Control | 33.2 | 0 | 32.0 |
| Control | 33.7 | 0 | 32.1 |
| 1 | 33.3 | 0 | 31.1 |
| 1 | 34.7 | 0 | 31.1 |
| 1 | 35.2 | 0 | 31.2 |
| 2* | 33.3 | 0 | 31.0 |
| 2* | 33.1 | 0 | 31.0 |
| 2* | 32.9 | 0 | 31.2 |
| 3 | 33.1 | 0 | 31.6 |
| 3 | 33.2 | 0 | 31.0 |
| 3 | 33.1 | 0 | 31.3 |
| 4 | 32.9 | 0 | 32.0 |
| 4 | 33.1 | 0 | 30.7 |
| 4 | 32.4 | 0 | 31.3 |
| 5 | 33.0 | 0 | 31.1 |
| 5 | 32.9 | 0 | 31.4 |
| 5 | 33.0 | 0 | 31.2 |
| 6 | 32.6 | 0 | 31.2 |
| 6 | 33.1 | 0 | 31.5 |
| 6 | 32.7 | 0 | 31.1 |
| 7 | 33.2 | 0 | 31.0 |
| 7 | 33.0 | 0 | 31.3 |
| 7 | 32.8 | 0 | 30.9 |
| PC (day 1) | 31.0 | 31.2 | 31.0 |
| NEG (day 1) | 0 | 0 | 31.1 |
| PC (day 2) | 30.5 | 31.2 | 31.0 |
| NEG (day 2) | 0 | 0 | 31.1 |

The fluid check problem relating to the female urine sample described above for HSV-1 also applied to HSV-2.

The table below presents Ct results of detecting the HSV-1 virus in the synthetic cerebralspinal fluid in the presence of the potential interfering substances.

| Interferent ID | HSV-2 (FAM ™) | HSV-1 (CFR610) | IC (Q670) |
|---|---|---|---|
| Control | 0 | 34.4 | 31.9 |
| Control | 0 | 33.5 | 32.2 |
| Control | 0 | 32.5 | 32.2 |
| Control | 0 | 34.0 | 32.3 |
| 1 | 0 | 35.0 | 32.4 |
| 1 | 0 | 33.3 | 31.7 |
| 1 | 0 | 32.9 | 31.9 |
| 3 | 0 | 34.2 | 31.7 |
| 3 | 0 | 34.4 | 31.2 |
| 3 | 0 | 33.6 | 31.7 |
| 4 | 0 | 35.0 | 32.1 |
| 4 | 0 | 36.4 | 31.4 |
| 4 | 0 | 36.7 | 31.5 |
| 6 | 0 | 35.5 | 32.2 |
| 6 | 0 | 33.5 | 31.4 |
| 6 | 0 | 34.3 | 32.5 |
| 7 | 0 | 33.9 | 33.1 |
| 7 | 0 | 36.1 | 32.6 |
| 7 | 0 | 33.8 | 32.9 |
| 8 | 0 | 34.4 | 31.7 |
| 8 | 0 | 33.4 | 31.6 |
| 8 | 0 | 32.1 | 31.3 |
| 9 | 0 | 34.1 | 31.7 |
| 9 | 0 | 32.6 | 31.4 |
| 9 | 0 | 32.4 | 32.0 |
| PC (day 1) | 31.0 | 31.2 | 31.0 |
| NEG (day 1) | 0 | 0 | 31.1 |
| PC (day 2) | 30.5 | 31.2 | 31.0 |
| NEG (day 2) | 0 | 0 | 31.1 |

The table below presents Ct results of detecting the HSV-2 virus in the synthetic cerebralspinal fluid in the presence of the potential interfering substances.

| Interferent ID | HSV-2 (FAM ™) | HSV-1 (CFR610) | IC (Q670) |
|---|---|---|---|
| Control | 34.2 | 0 | 32.4 |
| Control | 34.2 | 0 | 31.9 |

-continued

| Interferent ID | HSV-2 (FAM™) | HSV-1 (CFR610) | IC (Q670) |
|---|---|---|---|
| Control | 34.7 | 0 | 32.4 |
| Control | 34.6 | 0 | 32.3 |
| 1 | 34.6 | 0 | 31.5 |
| 1 | 36.0 | 0 | 31.5 |
| 1 | 36.3 | 0 | 31.2 |
| 3 | 34.3 | 0 | 32.3 |
| 3 | 33.5 | 0 | 32.1 |
| 3 | 34.5 | 0 | 32.1 |
| 4 | 33.4 | 0 | 32.0 |
| 4 | 34.0 | 0 | 31.5 |
| 4 | 33.2 | 0 | 32.2 |
| 6 | 34.0 | 0 | 32.4 |
| 6 | 34.6 | 0 | 31.8 |
| 6 | 33.3 | 0 | 31.8 |
| 7 | 34.1 | 0 | 31.9 |
| 7 | 35.1 | 0 | 31.7 |
| 7 | 34.0 | 0 | 32.6 |
| 8 | 33.3 | 0 | 31.6 |
| 8 | 33.6 | 0 | 31.4 |
| 8 | 32.6 | 0 | 31.9 |
| 9 | 34.0 | 0 | 31.8 |
| 9 | 34.0 | 0 | 31.2 |
| 9 | 33.1 | 0 | 31.9 |
| PC (day 1) | 31.0 | 31.2 | 31.0 |
| NEG (day 1) | 0 | 0 | 31.1 |
| PC (day 2) | 30.5 | 31.2 | 31.0 |
| NEG (day 2) | 0 | 0 | 31.1 |

The results were verified to be accurate based on a lack of valid amplification signal in the FAM™ fluorophores (Life Technologies) or CFR610 channels for the negative control and a Ct<40 in the Q670 channel. Also, the PC reactions gave a Ct<40 in the FAM™ fluorophore (Life Technologies) and CFR610 channels.

The results of the direct amplification assays for detecting HSV-1 and HSV-2 demonstrate that there was no significant change in Ct values with any of the interferents for either of the viruses tested. The direct amplification assays are therefore not affected by potential interfering substances when detecting low positive samples of these viruses.

Example 15: Components of Direct Amplification Assays Providing Improved Performance The following data represent components of the direct amplification assays that allow for improved performance. In one embodiment, a combination of all of these components provides a system that allows real time PCR to be effective even in the presence of known inhibitors (e.g., blood and heparin).

Effect of KCl

Figure 5:
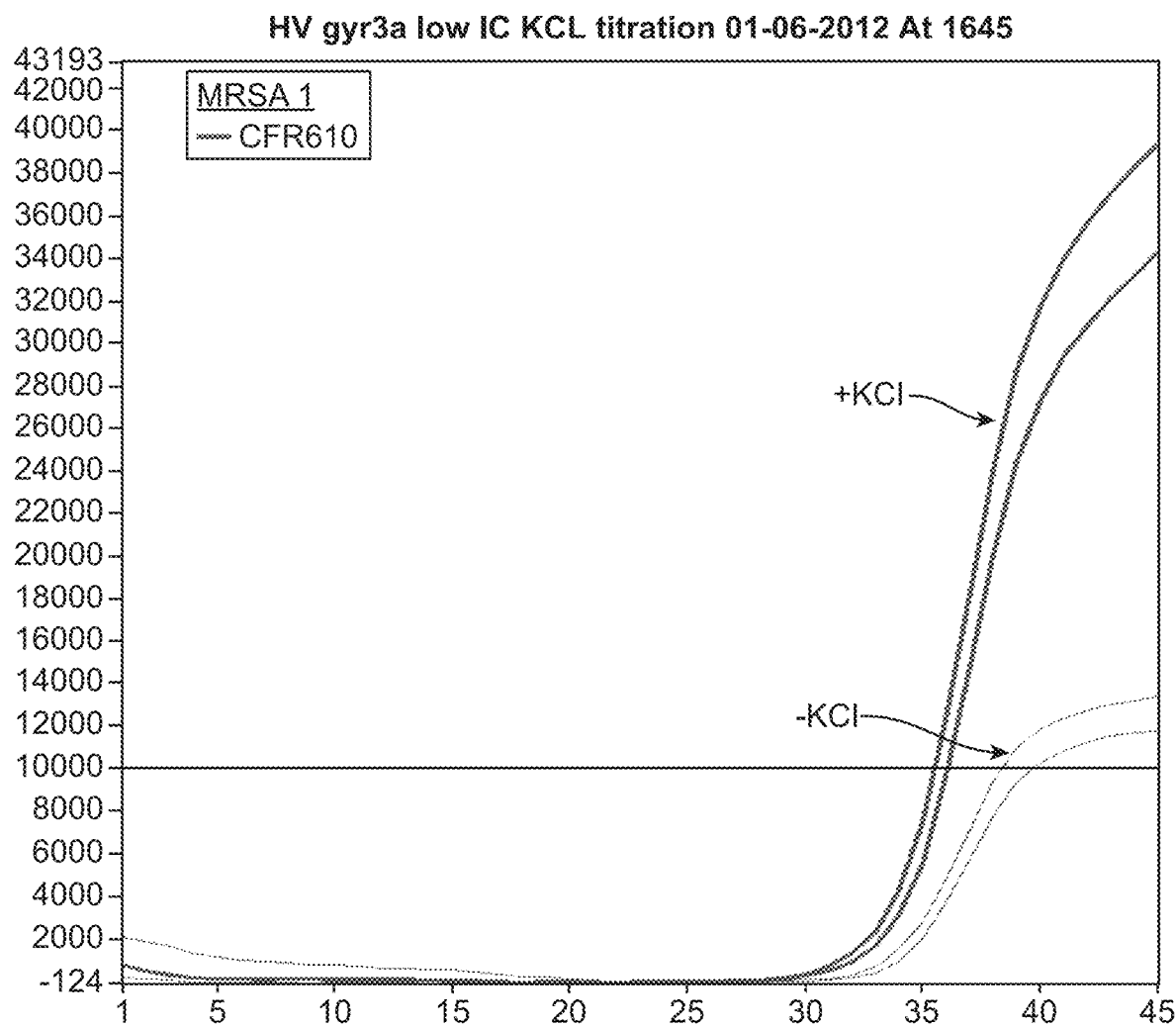
FIG. 5 is a line graph depicting the sensitivity of direct amplification assays with added KCl compared with direct amplification assays without KCl.

Adding KCl (up to 20-40 mM) to a direct amplification assay improves fluorescence signals and confers improved sensitivity to the reaction. The data in FIG. 5 demonstrates detection of MRSA in the presence and absence of KCl. Although some detection is possible without KCl, the presence of KCl improves the efficacy of the reaction. The data in FIG. 5 was generated in the presence of other reaction components, such as a cationic surfactant.

Effect of BSA

BSA was added to stool samples containing *C. difficile*, at various concentrations. At higher concentrations, represented by the 3500 ng/reaction below, inhibition was removed from some patient samples. As can be seen in the table below (presenting Ct values), at a lower 5 ng/reaction concentration of BSA, the *C. difficile* target was not detected and the internal control was missed in 2 out of 3 samples.

Specifically, the internal control was detected with Sample A. However, the lower Ct value, as compared with the sample at higher concentrations, demonstrates delayed amplification and is characteristic of inhibition (the Ct value is the PCR cycle at which sufficient signal is generated to detect the target in question).

| | BSA (3500 ng) | | BSA (5 ng) | |
|---|---|---|---|---|
| Sample | *C. diff* | Internal Control | *C. diff* | Internal Control |
| A | 34.30 | 30.30 | 0 | 35.70 |
| B | 34.10 | 31.90 | 0 | 0 |
| C | 33.90 | 33.20 | 0 | 0 |

Effect of Surfactants

Figure 6:
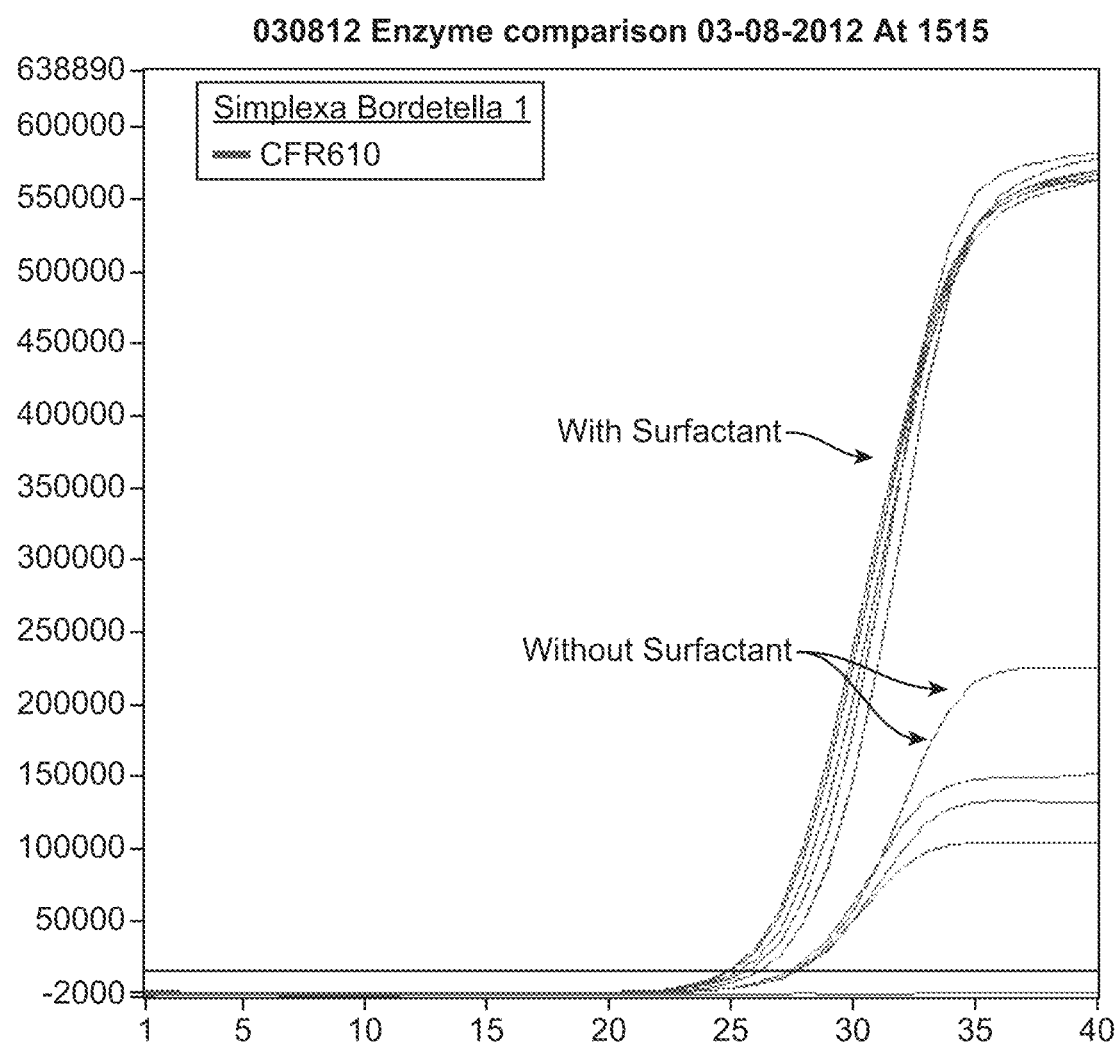
FIG. 6 is a line graph depicting the sensitivity of direct amplification assays with added surfactant compared with direct amplification assays without surfactant.

Adding cationic surfactants improves fluorescence signals and confers improved sensitivity to a direct amplification assay. As demonstrated in FIG. 6, in which a direct amplification assay was conducted on *Simplexa Bordetella*, some detection is possible without addition of the surfactant. However, when using the surfactant, efficacy of the reaction is improved, as demonstrated by greater signal height, which confers improved sensitivity.

Effect of Additional Heating

Figure 7:
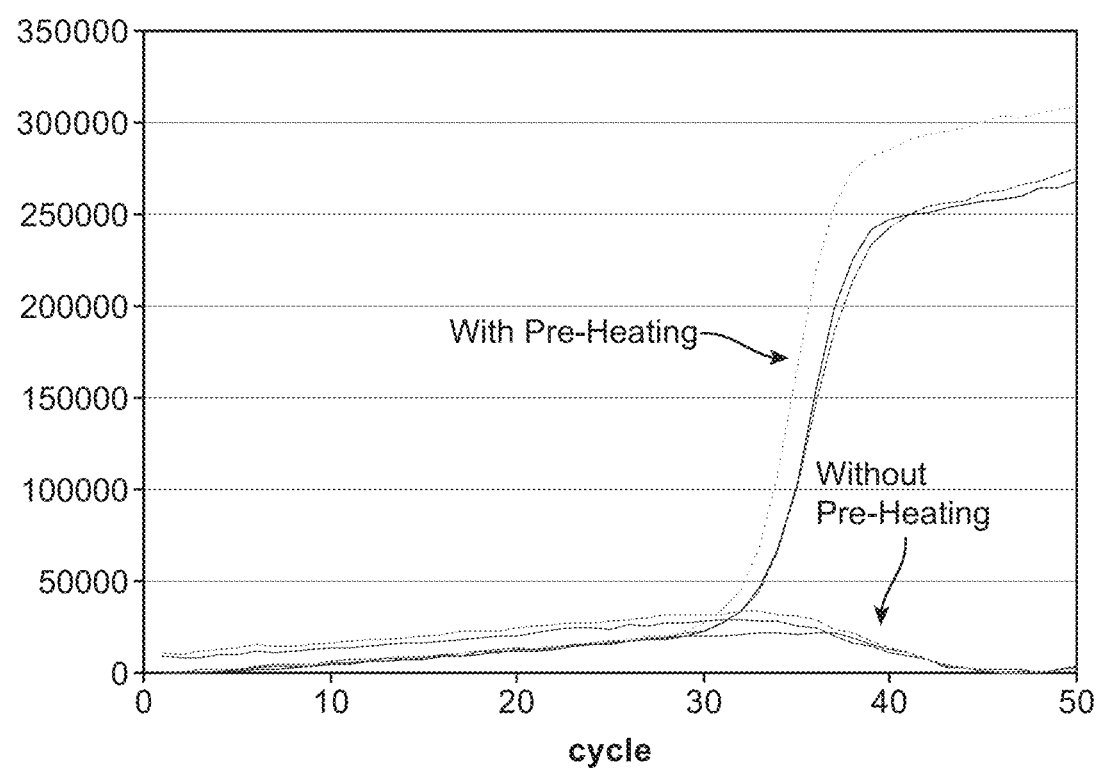
FIG. 7 is a line graph depicting the sensitivity of direct amplification assays with pre-heating compared with direct amplification assays without pre-heating.

Some organisms tested require additional heating steps to improve assay performance. For example, sensitivity improvements were observed for Flu B when using additional heating beyond that provided in a standard reaction (e.g., pre-heating), as demonstrated in FIG. 7. The improvement with Flu B was seen at a temperature of 70° C. Assay performance detecting other organisms, such as *C. difficile* and Group A *Streptococcus*, was seen at a temperature of 95° C. Heating the sample to destroy inhibitors and to lyse organisms must be balanced with the potential for heat to destroy reagents. In some embodiments, heating the samples is performed prior to adding the reagents (e.g., buffer).

Tolerance of System

The data below (*Bordetella pertussis/parapertussis* PCR) shows that the direct amplification assays can tolerate up to 30% transport media (Copan UTM) without inhibition. All samples tested below with direct detection methodology used a 30% sample and 70% direct amplification reaction mix. Results from direct detection were compared to results using DNA extraction and purification prior to amplification. The direct method had 99% sensitivity and specificity compared to the extraction and purification test using patient specimens.

| | Direct Detection Positive | Direct Detection Negative |
|---|---|---|
| Extracted Method Positive | 43 | 3 |
| Extracted Method Negative | 3 | 409 |

Previous publications required significant dilution prior to adding specimen to the reaction mixture, therefore limiting sensitivity.

Example 16: Direct Amplification Assays with Additional Specimen Types Whole Blood Whole blood was used to perform human genetic testing. Whole blood could be used with either a 1:4 dilution or with 0.5 µl in a 10 µl reaction volume. In either case, the heme (which is a known PCR inhibitor) did not affect the assay. Complete concordance was achieved when testing for the presence of Factor V Leiden mutations or Factor II mutations using the direct amplification method and when using the reference method which utilized nucleic acid extraction prior to amplification and mutation detection.

| | | Simplexa Direct FVL | | | |
|---|---|---|---|---|---|
| | | WT | HET | HOM | Total |
| REF | WT | 489 | 0 | 0 | 489 |
| | HET | 0 | 50 | 0 | 50 |
| | HOM | 0 | 0 | 4 | 4 |
| | Total | 489 | 50 | 4 | 543 |

| | | Simplexa Direct FII | | | |
|---|---|---|---|---|---|
| | | WT | HET | HOM | Total |
| REF | WT | 519 | 0 | 0 | 519 |
| | HET | 0 | 24 | 0 | 24 |
| | HOM | 0 | 0 | 0 | 0 |
| | Total | 519 | 24 | 0 | 543 |

Whole Blood with Heparin

Figure 8:
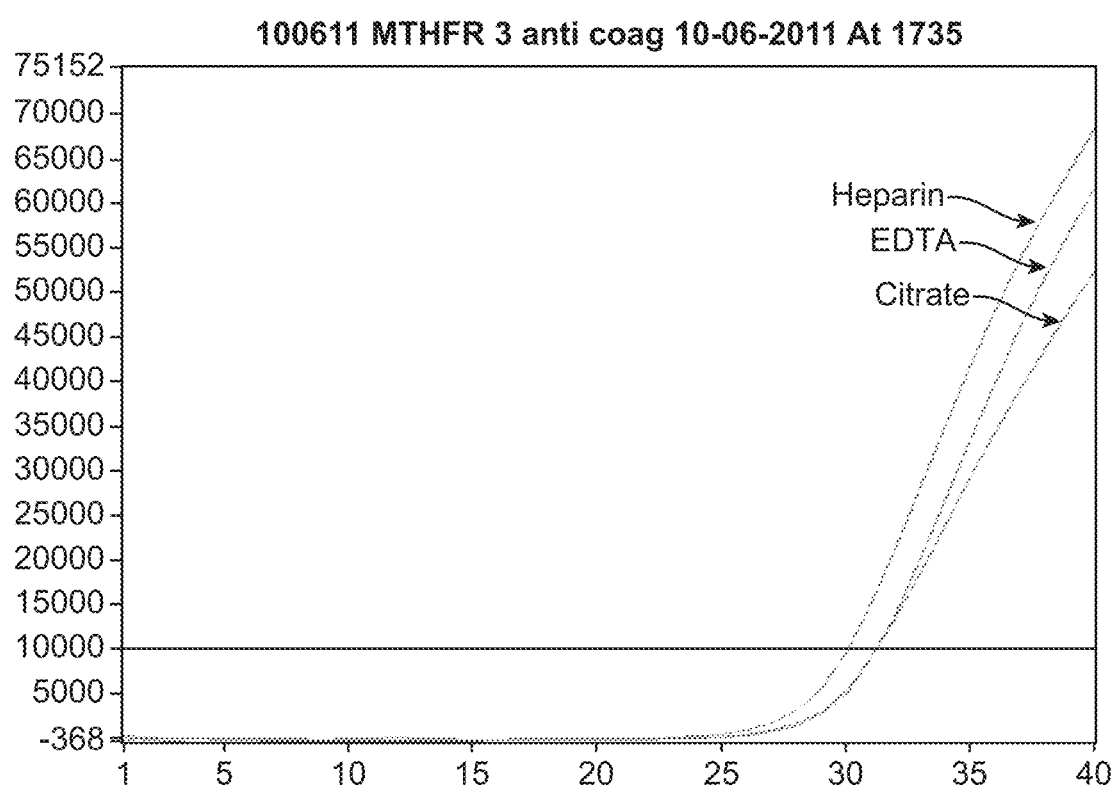
FIG. 8 is a line graph depicting amplification plots from a single blood sample that was exposed to a different anticoagulant in different tubes (heparin, EDTA, citrate).

The data in FIG. 8 shows amplification plots from a single blood sample that was collected into 3 tubes, each with a different anticoagulant (heparin, EDTA, citrate). As can be seen, the amplification plots show that all samples give efficient amplification, even when heparin, a known PCR inhibitor, is used as the anticoagulant.

Buccal Swabs

Figure 9:
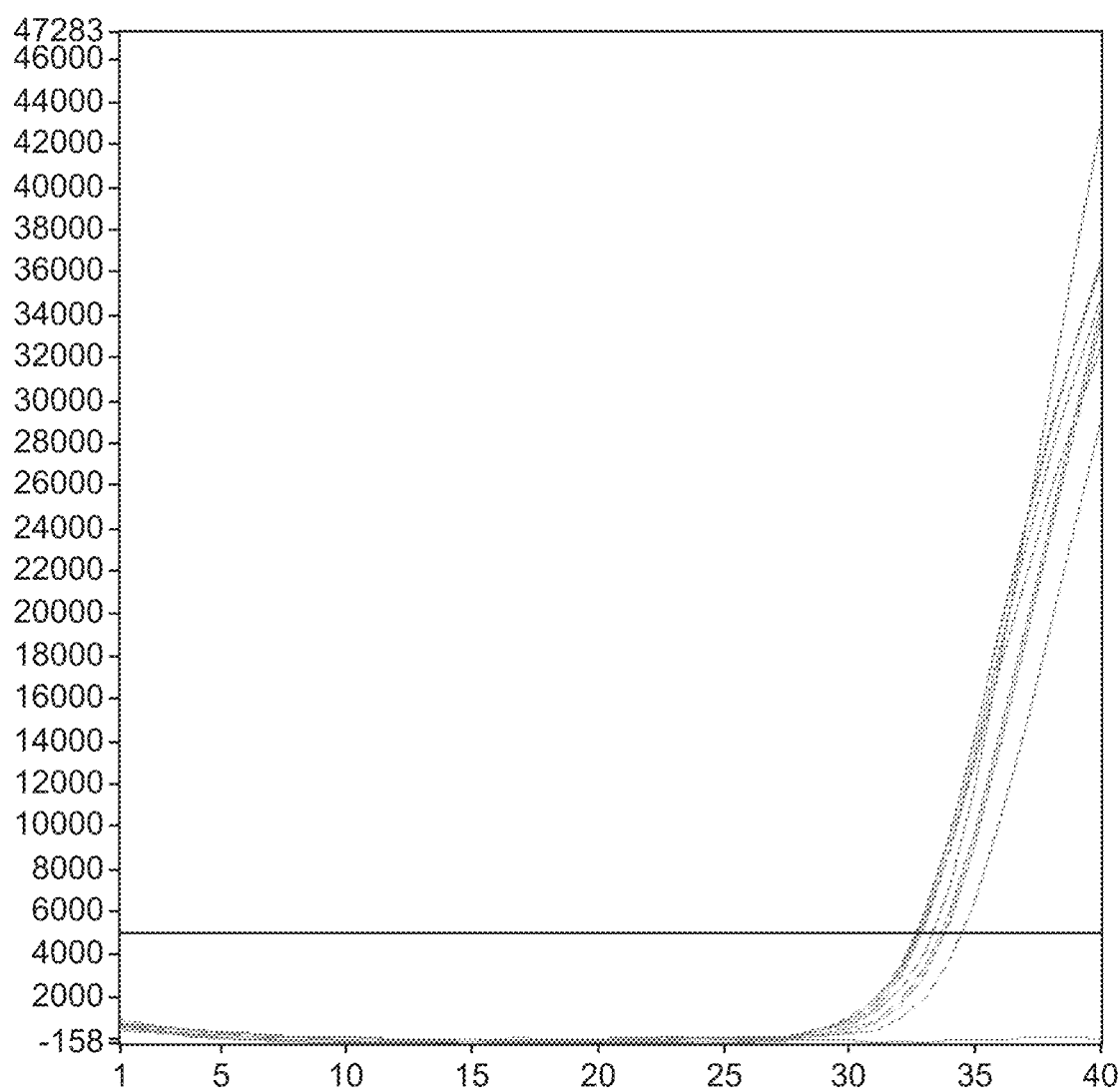
FIG. 9 is a line graph depicting the ability of direct amplification assays to detect samples from buccal swabs.

The data in FIG. 9 represents 4 replicates from each of 2 samples of human genetic DNA for mutations (detecting the Factor V Leiden mutation region), plus one negative control. Efficient amplification is seen for all replicates. Samples were collected by the swabbing inner cheek for about 10 seconds to ensure the whole swab surface was used. The swabs were then placed into 500 uL 1×TE Buffer 2 uL, which was loaded directly into the PCR sample without extraction.

Comparison to Previously Published Literature

Previously published results indicate that in order for effective detection, samples must be diluted. Compared to these publications, for example, the Pandori et al., BMC Infect. Dis., 6:104 (2006) reference, the foregoing data demonstrates a 10 fold greater amount of sample, providing a limit of detection that is 10 fold lower than the published method.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for identifying the presence or absence of a target nucleic acid from a microorganism in a biological sample obtained from a human, said method comprising:
   (a) contacting the biological sample with a reaction mixture containing a DNA polymerase and a buffer to form a sample mixture under conditions suitable for amplification of the target nucleic acid from the biological sample without extracting the target nucleic acid from the biological sample;
   (b) amplifying the target nucleic acid; and
   (c) identifying the presence of the target nucleic acid from the microorganism by detecting the amplified target nucleic acid,
   wherein the biological sample is prepared by mixing a swabbed specimen from the human in a buffer to produce the biological sample,
   wherein 20-30% of the total volume of the sample mixture following step (a) is the biological sample,
   wherein the swabbed specimen is from whole blood, plasma, serum, cerebrospinal fluid (CSF), or stool,
   wherein the nucleic acid in the biological sample is not extracted from the biological sample prior to amplification;
   wherein the target nucleic acid is not present in a biological sample that does not contain the microorganism; and
   wherein the reaction mixture contains a cationic surfactant.

2. The method of claim 1, wherein the biological sample is heated prior to step (a) or step (b).

3. The method of claim 1, wherein the reaction mixture comprises potassium chloride.

4. The method of claim 1, wherein the reaction mixture comprises albumin.

5. The method of claim 1, wherein the microorganism is a virus.

6. The method of claim 5, wherein the virus is selected from the group consisting of an influenza virus, a respiratory syncytial virus, a varicella zoster virus, a herpes simplex virus, and an enterovirus.

7. The method of claim 6, wherein the influenza virus is influenza Type A or influenza Type B.

8. The method of claim 6, wherein the herpes simplex virus is herpes simplex virus 1 (HSV-1) or 2 herpes simplex virus (HSV-2).

9. The method of claim 1, wherein the microorganism is a bacterium.

10. The method of claim 8, wherein the bacterium is *Clostridium* or *Streptococcus*.

11. The method of claim 10, wherein the bacterium is *C. difficile*.

12. The method of claim 10, wherein the bacterium is Group A *Streptococcus*.

* * * * *